United States Patent [19]

Ayres et al.

[11] Patent Number: 5,096,718
[45] Date of Patent: Mar. 17, 1992

[54] PRESERVING FOODS USING METABOLITES OF PROPIONIBACTERIA OTHER THAN PROPIONIC ACID

[75] Inventors: James W. Ayres; William E. Sandine, both of Corvallis; George H. Weber, Beaverton, all of Oreg.

[73] Assignee: The State of Oregon acting by and through the Oregon State Board of Higher Education on behalf of Oregon State University, Eugene, Oreg.

[21] Appl. No.: 192,231

[22] Filed: May 9, 1988

Related U.S. Application Data

[63] Continuation-in-part of Ser. No. 753,563, Jul. 10, 1985, abandoned, which is a continuation-in-part of Ser. No. 419,559, Sep. 17, 1982, abandoned.

[51] Int. Cl.$^5$ .......................... A23C 3/08; A23C 9/12; C12P 7/52
[52] U.S. Cl. .......................... 426/9; 426/34; 426/43; 426/61; 426/321; 426/330.2; 426/330.3; 426/330.5; 426/331; 426/334; 426/335; 435/141; 435/252.1; 435/822
[58] Field of Search .................. 426/9, 34, 43, 61, 321, 426/334, 330.2, 330.3, 330.5, 331, 335; 435/141, 252.1, 822

[56] References Cited

U.S. PATENT DOCUMENTS

| | | |
|---|---|---|
| 1,459,959 | 6/1923 | Sherman et al. .................. 435/42 |
| 1,470,885 | 10/1923 | Sherman et al. .................. 435/141 |
| 1,910,130 | 5/1933 | Sherman . |
| 1,937,672 | 12/1933 | Sherman .................. 435/141 |
| 2,154,499 | 4/1939 | Hoffman et al. . |
| 2,465,905 | 3/1949 | Meade et al. .................. 426/41 |
| 3,404,987 | 10/1968 | Kooistra et al. .................. 426/9 |
| 3,681,091 | 8/1972 | Kohl et al. . |
| 3,779,796 | 12/1973 | Vena et al. . |
| 3,812,269 | 5/1974 | Mueller et al. . |
| 3,846,567 | 11/1974 | Matyas et al. . |
| 3,895,116 | 7/1975 | Herting et al. . |
| 3,928,620 | 12/1975 | Courtade et al. . |
| 4,199,606 | 4/1980 | Bland . |
| 4,308,293 | 12/1981 | Tribble et al. .................. 426/532 |
| 4,497,883 | 2/1985 | Anderson .................. 435/141 X |
| 4,728,516 | 3/1988 | Boudreaux et al. .............. 435/43 X |
| 4,806,368 | 2/1989 | Reddy .................. 426/61 |

FOREIGN PATENT DOCUMENTS

| | | |
|---|---|---|
| 618210 | 4/1961 | Canada . |
| 1061632 | 9/1979 | Canada . |
| 1218894 | 3/1987 | Canada . |
| 0095268 | 11/1983 | European Pat. Off. . |
| 0096477 | 12/1983 | European Pat. Off. . |
| 2190365 | 1/1974 | France . |
| 71-2942 | 1/1972 | South Africa . |
| 1420237 | 1/1976 | United Kingdom . |
| 2060346 | 5/1981 | United Kingdom . |

OTHER PUBLICATIONS

Chung et al., "Growth of Salmonella at Low pH", *J. Food Sci.*, 35:326 (1970).
Compendium of Methods for the Microbiological Examination of Foods, "ASLA Agar for Propionibacteria", pp. 65 et seq. (1976).
The Condensed Chemical Dictionary, 10th ed., UNR, N.Y., 1981, p. 862.
Handbook of Food Additives, CRC Press, 2nd Ed., pp. 137–184 (1972).
Hettinga et al., "Pouch Method for Isolating and Enumerating Propionibacteria," *J. Dairy Sci.*, 51:1707–1709 (1968).
Hettinga et al., "The Propionic-Acid Bacteria—A Review", *J. Milk Food Technol.*, 35:295–301, 358–372, 436–447 (1972).
Ingle, "Some Preliminary Observations on the Effectiveness of Propionates as Mold Inhibitors on Dairy Products", *J. Dairy Sci.*, 23:509 (1940).
Isshiki et al., "Preservatives and Artificial Sweeteners", *J. Assoc. Off. Anal. Chm.*, 64:280–281 (1981).
Jackel et al., "A New Dried Dairy Culture Ingredient for Bakers", *The Bakers Digest*, Jun. 1975, pp. 38–39.
Johnston et al., "Incidence of Salmonella in Fresh Pork Sausage in 1979 Compared with 1969", *J. Food Sci.*, 47:1369–1371 (1982).
Kishishita et al., "New Medium for Isolating Propionibacteria and Its Application to Assay of Normal Flora of Human Facial Skin", *App. & Env. Microbiol.*, 10:1100–1105 (1980).
Kosikowski, *Cheese and Fermented Milk Foods*, published by author, Ithaca, N.Y., pp. 12, 15, 47–49, 235–330 (1966).
Kriek et al., "Toxicity of Penicillium Italicum to Laboratory Animals", *Fd. Cosmet. Toxicol.*, 19:311–315 (1981).
Langsrud et al., "Flavor Development and Microbiology of Swiss Cheese—A Review: I. Milk Quality and Treatments", *J. Milk Food Technol.*, 36:487–490 (1973).
Langsrud et al., "Flavor Development and Microbiology of Swiss Cheese—A Review: II. Starters, Manufacturing Processes and Procedures", *J. Milk Food Technol.*, 36:531–542 (1973).

(List continued on next page.)

Primary Examiner—David M. Naff
Attorney, Agent, or Firm—Klarquist, Sparkman, Campbell, Leigh and Whinston

[57] ABSTRACT

A metabolite material of propionibacteria, having a metabolite of molecular weight greater than 300, is added to a food product to inhibit the growth of gram negative psychotropic bacteria, yeast, mold, gram positive bacteria, or Listeria. The metabolite material may contain less than 0.02% propionic acid such that there is insufficient propionic acid per se to inhibit microbial growth. The metabolite material is produced by growing propionibacteria cells in a liquid growth medium to produce a mixture containing the metabolite material. The mixture can be concentrated and added to a food product as a concentrated liquid or powder. The metabolite material added to a food product may contain viable cells of propionibacteria.

14 Claims, No Drawings

OTHER PUBLICATIONS

Langsrud et al., "Flavor Development and Microbiology of Swiss Cheese—A Review: III. Ripening and Flavor Production", *J. Milk Food Technol.*, 36:593–609 (1973).

Langsrud et al., "Flavor Development and Microbiology of Swiss Cheese—A Review: IV. Defects", *J. Milk Food Technol.*, 37:26–41 (1974).

Lee et al., "Diacetyl Production by Propionibacterium Shermanii in Milk Cultures", *Canadian J. Microbiol.*, 16:1231–1242 (1970).

Macy, "Mold Inhibitors for Food Products", *Assn., Food & Drug Officials, Quart. Bul.*, 6:9–12 (1942).

Majchrzak et al., "Studies on Bread Preservation and Enrichment in Vitamins B12 & Calcium, Part I", *Technol. Riono-Spozyw, (Zeuz. Nauk Szh. Gl. Gospod. Wiejsk. Akad. Roln. Warszawie) 12:23–35 (1977)*.

Malik et al., "An Evaluation of the Taxonomy of Propionibacterium", *Canadian J. Microbiol.*, 14:1185–1191 (1968).

Marsili et al., "High Performance Liquid Chromatographic Determination of Organic Acids in Dairy Products", *J. Food Sci.*, 46:52–57 (1981).

*The Merck Index*, 9th ed., p. 7614 (1976).

Miller, "Mold Growth on Cheddar Cheese and Its Control", *Proceedings, Institute of Food Technol.*, 1:153–158 (1940).

Nieuwenhof, "Stimulating Effect of Lactobacilli on the Growth of Propionibacteria in Cheese", *Neth. Milk Dairy J.*, 23:287–289 (1969).

O'Leary et al., "Development of B. Mesentericus in Bread and Control with Calcium Acid Phosphate or Calcium Propionate", 18:730–740 (1941).

Olson et al., "Propionic Acid and Its Calcium and Sodium Salts as Inhibitors of Mold Growth", *J. Dairy Sci.*, 23:509–510 (1940).

Reynolds et al., "Bactericidal Properties of Acetic and Propionic Acids on Pork Carcasses", *J. Animal Sci.*, 38:515–519 (1974).

Skogen, "Capsulation of Propionibacterium", Iowa State University Master's Degree Thesis, pp. 69–71 (1970).

Suryarachchi et al., "Occurrence and Growth of Yeasts in Yogurts", *App. & Env. Microbiol.*, 42:574–579 (1981).

Vedamuthu, "The Use of Candle Oats Jar Incubation for the Enumeration, Characteristization, and Taxonomic Study of Propionibacteria", *Milchwissenshaft*, 22:428–431 (1967).

Wolford et al., "Propionates Control Microbial Growth in Fruits, Vegetables", *Food Indus.*, 17:622–624, 726, 728, 730, 732, 734 (Jun. 1945).

Bhunia, et al., "Direct Detection of an Antimicrobial Peptide of *Pediococcus aidilactici* in Sodium Dodecyl Sulfate-Polyacrylamide Gel Electrophoresis", *J. Indust. Microbiol. 2:1b–4b(1987)*.

Jenness, et al., Principles of Dairy Chemistry, Chapman & Hall, N.Y., 1959, pp. 370–375.

Lindsay, et al., "Identification of Volatile Flavor Components of Butter Culture" *Journal of Dairy Science*, Dec., 1965, vol. 43, No. 12, pp. 1566–1574.

PRESERVING FOODS USING METABOLITES OF PROPIONIBACTERIA OTHER THAN PROPIONIC ACID

CROSS REFERENCE TO RELATED APPLICATION

This is a continuation-in-part of application Ser. No. 753,563, Filed July 10, 1985, now abandoned which is a continuation-in-part of application Ser. No. 419,559, filed Sept. 17, 1982, now abandoned. Each of the prior applications is incorporated herein by reference.

BRIEF SUMMARY OF THE INVENTION

The present invention relates to chemical substances which affect microbial growth. More specifically, it relates to substances which inhibit spoilage microorganisms in food products.

The need for improved methods of food and feed preservation is great; activities of bacteria, molds, and yeasts render millions of pounds of food inedible annually and the problem is especially acute in countries with inadequate refrigeration. Each of these microorganisms has different biochemical and nutritional needs such that materials which inhibit one type often do not inhibit the others. Among spoilage microorganisms, the yeasts and molds are economically the most significant because they are so versatile from nutritional and growth-temperature standpoints and because their spores are so ubiquitous. Yeasts are often the most difficult to inhibit. Minimizing their effects in food presently depends on asepsis and sanitation, exclusion of oxygen and use of chemical additives (Ayres, Mundt and Sandine, *Microbiology of Foods*, W. H. Freeman and Co., 1980, p. 140).

For some foods, bacteria are more important spoilage agents than yeasts or molds. Cottage cheese and market milk products such as pasteurized whole milk, skim milk, half and half, and whipping cream are examples of such products. Psychrotrophic bacteria, able to grow at refrigeration temperatures (35° to 50° F.), rapidly spoil these products in the commercial marketplace.

Propionibacteria are known to produce propionic acid and a large amount of propionic acid is produced by a specific propionibacteria (*Propionibacterium acidipropionici* #B3568-Anderson, U.S. Pat. No. 4,497,383). Propionic acid ($CH_3CH_2COOH$-*The Merck Index, 9th ed., Merck and Co., Inc.*, 1976) is known as a mold inhibitor, but is not known as a useful inhibitor of yeasts or bacteria in amounts which can be added to foods commonly spoiled by yeasts and bacteria. Propionic acid has a distinct, unpleasant taste and stimulates the gag or vomiting reflex at concentrations lower than other similar organic acids such as acetic acid or citric acid. It does find use to inhibit only mold in stillage (Draughon et al., *J. Food Sci.* 47:1018, 1982), bread and in certain food wrappers for use outside the food, such as those for cheese (Ayres et al., *Microbiology of Foods*, W. H. Freeman and Co. 1980, p. 140; Moon, *Proc. Am. Soc. Microbiol.*, 1981, p. 29).

Fermentation broth concentrations of propionic acid of >0.5% and preferably >1.3% are usually reached with the unique propionibacterial species *Propionibacterium acidiprooionici* #B 3568 (Anderson, U.S. Pat. No. 4,497,383). Mycostatic activity (mold inhibition) is reported to be directly proportional to the propionic acid produced in the fermentation process. A control fermentation of *P. shermanii* produced 0.80% propionic acid and 0.39% acetic acid for a total of 1.19% acids while the unique species *P. acidipropionici* was superior as a mycostatic agent by producing 0.96% propionic acid and 0.20% acetic acid for a total of 1.16% acids; that is, Anderson teaches that the propionic acid is a mycostat and the acetic acid was of little significance. He suggests that fermentated whey containing these amounts of propionic acid can be substituted for pure propionic acid as a mycostatic agent and incorporated into breads, pastries and other bakery products.

A report from Poland also shows that propionic acid produced by propionibacteria can be substituted for chemically produced propionic acid to inhibit mold in bread (Agric. Acad., Inst. Food Technol., Warsaw, Pol., *Zesz. Nauk. Szh. Gl. Gospod. Weijsk. Ikad, Roln, Warszagie, Technol. Riono-Spozvw.*, 12, pp. 23-26, 1977 [pubs. 1978]). After fermenting whey with *Propionibacterium petersonii* T-112 and incorporation to make bread, they found the flour contained 0.85% propionic acid and 0.34% acetic acid, and mold appearance was inhibited. They state that the bread contains at least twice the amount of propionic acid recognized to inhibit mold and suggest "future studies should involve lesser amounts of propionate (0.2% of the flour)". The findings of Anderson and the Polish article are not surprising since propionibacteria are known to produce >0.5% propionic acid, and concentrations >0.2% are known as the amount needed to inhibit mold.

The suggestion of Anderson and the Polish article that propionic acid produced by propionibacteria is in high enough concentrations to preserve bread against mold spoilage provides no useful information about inhibition of gram negative psychrotrophic bacteria because such bacteria are never spoilage organisms in bread. Yeast, of course, also are not spoilage microorganisms in bread.

Wolford et al. show that propionic acid is not useful to inhibit yeasts or bacteria in foods ("Propionates Control Microbial Growth in Fruits, Vegetables", *Food Industries*, 17: 622-625, 726, 728, 730, 732, 734 (June 1945)). Experiments involving dipping of lima beans in 5 percent sodium propionate solution inhibited bacterial growth for a number of hours, (same for peas). Such inhibition of bacteria for a few hours with such a high concentration of propionate is meaningless for food preservation. The authors also state "propionates should be used with due regard to its limitations, such as the pH of the product, its microbial flora, and the concentration of propionate likely to impart foreign flavor or odor to the food."

Wolford et al. also reported concentrations of 2.0 percent propionic acid were needed to inhibit *Saccharomyces ellipsoideus* yeast and concentrations of 3.0 percent were needed to inhibit *Saccharomyces cerevisiae* yeast. Thus, low concentrations were not effective against yeast. Apple slices were treated with only 0.5% calcium propionate solution and these "proved to be less susceptible to damage by molds than were similar slices not treated with propionate. However, the fruit carried a propionic odor and tended to become more noticeably gray than did untreated slices".

An authoritative text (*Handbook of Food Additives*, 2nd ed., CRC Press, 1972, pp. 137-141) references the work of Wolford et al. and then those who wrote this section in the CRC Handbook reviewed other long known appropriate literature on propionic acid, sodium propionate and calcium propionate and concluded that "propionates are more active against molds than sodium benzoate, but have essentially no activity against yeasts. They have little action against bacteria with notable exception of their ability to inhibit the organisms which cause rope". It is also reported that propionates "are suitable for yeast-raised as well as other baked goods" and "because propionates inhibit molds and spares yeast" they are used in breads (the *Handbook of Food Additives,* 2nd ed., CRC Press, 1972, pp. 137-141).

Microbial metabolites, such as bacteriocins and especially so-called antibiotics, which inhibit the growth of microorganisms are well-known. Indeed, a large segment of the pharmaceutical industry is based on the sale of purified anti-microbials which find uses in medicine and to some extent also in the food industry. Lactic streptococci are commonly used in dairy fermentations to produce cheeses. An article by Geis et al. (Geis, Singh and Teuber, "Potential of Lactic Streptococci to Produce Bacteriocin", Applied and Environmental Microbiology, Jan. 1983, p. 205-211) showed that about 5% of 280 strains investigated produced bacteriocin. It is significant that none of the bacteriocins acted on gram-negative bacteria.

A considerable body of literature exists on propionibacteria which produce propionic acid. Their metabolites are not known to inhibit either bacteria or yeasts. In fact, Anderson (U.S. Pat. No. 4,497,833) states that the metabolites which contain enough propionic acid to inhibit mold can be used to grow yeasts in bread production. Meade and Stringham (U.S. Pat. No. 2,465,905) use a mature culture of mixed metabolites of *Propionibacterium shermanii* as a nutrient broth to grow bacteria (*Lactobacillus bulgaricus*). The propionibacteria do not inhibit the Lactobacillus bacteria but do impart a distinctive flavor to the final product (Column 3, lines 45-48). Meade teaches that propionates do not inhibit bacterial growth (Column 3, lines 47-52). James Sherman (U.S. Pat. No. 1,937,672) also shows the growth of a bacterium (*Lactobacillus casei*) with Bacterium acidipropionici, and states that bacteria other than the *Lactobacillus casei* can be used with propionibacteria (Column 2 [right side]-lines 125—132). Thus, it is clear that mixed metabolites of propionibacteria are not known to inhibit bacteria but are used to support their growth.

Early literature (Shaw and Sherman, *J. Dairy Sci.* 6:303, 1923) reported that propionibacteria produced acetic and propionic acids. The production of other volatiles, namely acetaldehyde, propionaldehyde, ethanol, propanol and dimethyl sulfide, by these bacteria was noted by Keenan and Billis (*J. Dairy Sci.* 51:797, 1968). Diacetyl production by propionibacteria was reported by Lee et al. (*Can. J. Microbiol.* 16:1231, 1970). The Handbook of Food Additives, 2nd ed., (*CRC Press,* 1972), pp. 137-141, provides background information on propionic acid and its salts, including uses. physical and chemical properties, antimicrobial activity, safety, regulatory status, applications, handling, storage and assay. The same type of information on acetic acid and acetates is presented in this reference on pages 147-150. Propionibacteria are known to also produce succinic acid as well as acetic acid (Wood and Wekman, "Mechanism of Glucose Dissimilation by the Propionic Acid Bacteria," *Biochem. J.* 30:618-623, 1936; Wood and Wekman, "The Relationship of Bacterial Utilization of $CO_2$ to Succinic Acid Formation", *Biochem. J.* 34:129-137 (1940); Leaver, Wood and Stjerholm, "The Fermentation of Three Carbon Substrates by *C. Propionicum* and *Propionibacterium*", *J. Bacteriol.* 70:521-530, 1955. As mentioned above, these metabolite mixtures from propionibacteria cultures have been used as nutrient baths to grow bacteria.

Acetic acid is the main constituent of vinegar and has a definite characteristic odor and flavor. The *Handbook of Food Additives,* 2nd ed., (CRC Press, 1972), refers to work which shows that homologs of propionic acid (such as succinic) have tastes and odors which would be noticeable in foods such as baked goods. Therefore, it is not anticipated that a nutrient growth medium containing propionibacteria or their metabolites could be used as a liquid suspension, or especially after concentrating or drying as an additive to unbaked foods or feeds without producing an undesirable change in flavor or odor. For baked goods, volatiles and some short chain organic acids and flavor producers may escape during the high temperatures used. As described earlier, Meade and Stringham indicate that propionibacteria metabolites produce a distinctive flavor to animal feeds, even without concentration. Propionibacteria are used in the production of Swiss cheese but only a very small amount of propionibacteria (only about 10% of the total inoculum or 0.1% of the milk used) produces distinctive flavor characteristics.

Propionibacteria are reported to produce an antiviral component (Ramanathan, Read and Cutting, "Purification of Propionin, An Antiviral Agent from Propionibacteria", *Proc. Soc. Exp. Biol. Med.* 123:271-273, 1966; Ramanathan, Waynec and Cutting, "Antiviral Principles of Propionibacteria", Isolation and Activity of Propionics B and C, *Proc. Soc. Exp. Biol. Med.* 129:73-77, 1968.

Despite the many reported techniques in the art of food preservation and a great deal of ongoing research concerning propionates and propionibacteria, there was until now no simple, natural additive substance that could effectively inhibit such difficult spoilage microorganisms as yeasts, molds, gas producing bacteria, Listeria, and, particularly, slime-producing psychrotrophic bacteria.

It is now discovered, quite surprisingly, that a mature propionibacterium growth medium can provide prolonged inhibition of yeasts, gram negative bacteria, some gram positive bacteria, and mold. This effect can occur without providing an undesirable flavor, odor, or appearance, even in "delicate" foods. A process has been discovered for preserving various foods comprising use of a propionic acid bacterial fermented material which provides insufficient propionic acid to preserve the food. Of particular significance, it has been found that propionibacteria produce one or more metabolites other than propionic acid such that, in combination, components of the mature growth medium have a greater inhibitory effect on food spoilage yeast, or gram negative psychrotrophic bacteria, or the gram positive pathogen *Listeria monocytogenes,* or gas producing bacteria, or mold than a weight of pure propionic acid equal to the pure propionic acid content of the mature growth medium. The unexpected findings disclosed are especially dramatic in light of the breadth of activity and some of the low concentrations which provide microbial inhibition.

The type of activity found for the unidentified metabolite or metabolites of propionibacteria is surprising in comparison to antimicrobial metabolites of other microorganisms. Nisin, for example, is an inhibitor of mold produced by *Streptococcus lactis.* Although it is an excellent inhibitor of mold, nisin is not inhibitory against yeasts, fungi or gram-negative organisms (Alfred Larry Brannen and P. Michael Davidson, *Antimicrobials in Foods*, Marcel Dekker, 1983, 332). Other bacteriocins produced by *Streptococcus lactis* and *Streptococcus cremoris* can be divided into four types and show activity against some gram positive bacteria but none of the bacteriocins acted on gram-negative bacteria (Geis, Singh and Tenber, "Potential of Lactic Streptococci to Produce Bacteriocin", Applied and Environmental Microbiology, Jan. 1983, pp 205-211). Other antimicrobials are also known to be fairly specific, such as vancomycin (active only against gram-positive bacteria at clinically achievable concentrations) and polymyxin B sulfate for gram-negative bacilli (all gram-positive bacteria, fungi and gram-negative cocci are resistent). Nystatin and Amphotericin B are antifungal agents with no appreciable activity against bacteria. Griseofulvin is fungistatic against Microsporum, *Epidermophyton and Trichophyton but has no effect on bacteria or other fungi* (*Drug Facts and Comparisons*, J. B. Lippincott, St. Louis, Mo., 1988, pp. 1459, 1490, 1491, 1499, 1505 and 1508). Thus, many antimicrobial metabolites are narrow in their action. Propionibacteria are known to produce propionic acid; and propionic acid in sufficient concentrations is known to inhibit mold. It is consistent with the above examples that this known metabolite of propionibacteria (propionic acid) is relatively narrow in its action and is not used to inhibit yeasts or bacteria by addition into food products although it is used in bread to inhibit mold. It is now shown that propionibacteria produce one or more previously unknown metabolites other than propionic acid which surprisingly have activity against gram negative bacteria, some gram positive bacteria, yeasts and molds.

An antimicrobial food additive can be obtained by growing propionibacteria, e.g. *Propionibacterium shermanii, P. freudenreichii, P. pentosaceum, P. thoenii, P. arabinosum, P. rubrum, P. jensenii, P. peterssonii*, and related species (as identified in Malik et al., *Can. J. Microbiol.* 14:1185, 1968) in a milk, cheese whey or broth medium or other suitable nutrient mixtures. The resulting growth liquid is then added to food and feed products to inhibit yeasts, molds and spoilage bacteria. To facilitate storage and shipment, the growth liquid may be dried to form a powder, or frozen before use as an antimicrobial food additive. The metabolites may be separated or purified or used as a mixture. Powdered or liquid natural metabolites of propionibacteria can be incorporated into various foods and feeds to render them less susceptible to spoilage by growth and/or enzymatic activity of yeasts, molds and bacteria. Antimicrobial activity may be obtained by incorporating viable propionibacteria directly into a food.

The growth medium for such Propionibacterium species may be formulated with milk or whey containing yeast extractives or fruit juices or any other broth media containing appropriate growth nutrients. The growth liquid, after development of the propionibacteria up to $10^6$ to $10^{10}$ cells per ml, may be heat treated (pasteurized) to kill the inoculated and adventitious bacteria prior to use in liquid, condensed, dried, or frozen form. It is added in various concentrations (preferred between 0.01 and 10% of total weight) to food or feed where it functions to inhibit yeasts, molds or certain bacteria. This inhibition enables the shelf life and storage times of the food or feed to be increased.

These findings are surprising and have not previously been taught, because they have not been known. It has been known that propionic acid, when used in a significant amount, inhibits mold, and it has been known that propionibacteria produce propionic acid. It is even stated in Anderson and the Polish article that propionibacteria produce sufficient propionic acid to inhibit mold. It is not recognized or suggested, however, that mixture of propionibacteria metabolites can be more inhibitory to mold than is due to the propionic acid produced. In fact, Anderson states that the mycostatic activity is directly proportional to the propionic acid, and the Polish article suggests that the metabolites should be used to produce 0.2% propionates in flour to inhibit mold. This literature suggests that metabolite mixtures would be required in sufficient amounts to provide at least 0.2% propionates.

According to the present invention, certain mixtures of propionibacterial metabolites can inhibit mold or preserve against mold when there is insufficient propionic acid present to preserve. More specifically, this effect can be obtained when the final propionic acid concentration is considerably less than 0.2%, which is reported to be the minimum effective amount of propionic acid. Following the method of the present invention, an equivalent degree of inhibition has been obtained in samples where there is less than 0.02% propionic acid present. This is a tenfold improvement.

Such an improvement is of major significance in the food industry. In the production of large quantities of foods, use of one-half as much ingredient represents a major savings. In considering fermentation processes, such as a process for producing metabolites of propionibacteria, the need to produce only one-half as much product can represent millions of pounds of product. A 50% reduction in usage is a monumental improvement in an industry where a change of 16% is considered a major advance (see Anderson patent [0.96% vs. 0.80%] propionic acid production). For example, assume a propionibacteria metabolite mixture contains 1% propionic acid and 0.2% is the usual amount utilized to inhibit mold. This means that a food product preserved with the propionibacteria metabolite mixture would need to contain 20% of the metabolite mixture. This amount is totally unacceptable for use with such foods as sour creams, cottage cheese, yogurt or sausage meats. Thus, the finding that the metabolites of propionibacteria inhibit mold in a food product even when they provide less than 0.2% propionic acid in the food product is very useful. The finding that preservation occurs when the metabolites provided less than 0.1% is more than twice as useful, and it is even more than ten times as useful when only 0.02% propionic acid is needed, especially when the mixture has been concentrated.

Propionibacteria grow in about 7%-11% solids medium (Anderson, U.S. Pat. No. 4,497,833; Polish article) to produce a maximum of about 1.4% propionic acid. If this mixture is concentrated to dryness with no loss of propionic acid, it would contain about 20% propionic acid. Thus, it would be expected to inhibit mold if 1% of the dried, concentrated metabolites were incorporated into a food product. In the processes of the present invention, however, the amount of concentrate needed is only about ½ to about 1/10 what was previously thought to be the minimum.

It is therefore a general object of the present invention to extend the shelf life of food products subject to microbial spoilage.

An important object is to provide a substance which can be added to a food product to inhibit the growth of mold, yeast and some bacteria without harming the flavor, aroma, or other characteristics of the food product.

A specific object is to extend the shelf life of dairy foods, cultured foods, high acidity foods, and specifically cottage cheese, yogurt, Kissel-type products, fruit juice, salad dressings, pasta, sausages, and other meat products such as chicken, fish, crab, hamburger or others.

An additional object is to provide a method which uses naturally produced substances in the preservation of food and feed.

A related object is to provide such a method which uses only a small quantity of such naturally produced substances.

Further an object of the present invention is to provide such a method to inhibit microorganisms which are potentially injurious to human health.

It is also an object to provide antimicrobial substances which can be maintained in a dried or frozen form for simplicity of storage and shipment.

In certain embodiments, it is an object to provide an antimicrobial food additive substance comprising a growth mixture containing bacteria and metabolites thereof, with the bacteria being viable or made not viable depending upon whether it is desired to produce additional amounts of metabolites, including $CO_2$, after the antimicrobial substance is added to the food product.

Still another object is to provide a growth medium in which propionibacteria can grow and produce metabolites having properties that effect the growth of other microbes.

These and other objects will become increasingly apparent by reference to the following description.

DETAILED DESCRIPTION

For the purpose of this disclosure, "metabolite" is defined as a substance, other than water, produced by propionibacteria. An "active metabolite" or an "inhibitory metabolite" is metabolite which inhibits the growth or reproduction of an undesired microorganism.

There are several aspects to the present invention as set forth below. It has been found possible to inhibit spoilage microorganisms and thereby extend the shelf life of many food products without adversely affecting flavor or aroma by adding a growth mixture containing a propionibacterium culture with its metabolites or a fraction of such a growth mixture which fraction contains one or more inhibitory metabolites other than propionic acid. The mixture or fraction has a greater inhibitory effect than a weight of pure propionic acid which is equal to the pure propionic acid content of the mixture or fraction. Such substances, which should be widely accepted as safe for human consumption, are surprisingly excellent inhibitors of spoilage microorganisms.

Examples of the present invention are set forth hereinafter. It is intended that they be only illustrative. Propionibacterium strains identified by number are available from the American Type Culture Collection (ATCC). The other cultures are widely available or can be obtained from Oregon State University, Corvallis, Oreg., without cost.

MIXED METABOLITES OF PROPIONIBACTERIA

It is discovered that Propionibacterium cultures can be used to produce a preservative material, including one or more metabolites (other than simple carboxylic acids, such as acetic acid, succinic acid and propionic acid) that inhibit mold, yeast, and certain food spoilage bacteria in any of a wide variety of food products. A food product is preserved by providing in or on the product one or more of such active metabolites.

For certain propionibacterial growth mixtures, some inhibition of spoilage microbes may be partially due to the presence of propionic acid as a metabolite of propionibacteria. But, the degree of inhibition achieved may be much greater than is due to the amount of propionic acid in the mixtures of metabolites studied. In some cases where excellent inhibition occurs, the amount of propionic acid is so low as to have no measurable effect at all. This indicates that some other inhibitory substance or substances (identified by a high molecular weights of >300) in propionibacteria growth mixtures is responsible for the excellent ability of such growth mixtures to extend the shelf life of food products.

Preservative materials according to the present invention contain one or more of such high molecular weight substances, perhaps along with propionic acid. Such materials have a greater inhibitory effect than could be achieved by their propionic acid contents alone.

As mentioned above, very small amounts of viable propionibacteria are used in the manufacture of Swiss cheese to form eyes by the production of $CO_2$ and to impart the characteristic Swiss cheese flavor. In most food products, however, the presence of viable propionibacterial would be unacceptable because eyes would not be desired and a $CO_2$ release may bloat packaging materials. Thus, as described in certain of the following examples, Propionibacteria can also be grown in a liquid growth medium which is subsequently heated or otherwise treated to render the bacteria not viable. The result is a stable material which is an effective additive for the inhibition of spoilage bacteria in food products.

To facilitate storage and shipping, a propionibacteria growth mixture may be frozen or concentrated, e.g. by spray-drying, or freeze-drying, to form a powder.

A preservative material according to the present invention is most readily used by mixing with a bendable food product, but should also be effective to treat the surface of solid food products, or the interior of such products, e.g. by injection. The optimum amount to be used will depend on the composition of the particular food product to be treated, but can be determined by simple experimentation.

In most instances, substantial improvements in shelf life can be obtained by adding the preservative material in an amount sufficiently small that it will have no deleterious effect on the flavor or aroma of the food product. This is possible because the material includes at least one high molecular weight propionibacteria metabolite which is active in inhibiting spoilage organisms and does not impart a strong flavor such as that of propionic acid.

Example 1 illustrates, generally, the effectiveness of propionibacteria growth mixtures as preservative materials.

EXAMPLE 1

This example shows that propionibacteria can produce metabolites which are inhibitory to a variety of gram negative microorganisms. Examples which follow show that metabolites other than propionic acid are inhibitors of the gram negative microorganisms. All gram negatives tested are food spoilage organisms which were isolated from spoiled cottage cheese.

100 ml bottles of non-fat milk fortified with 0.1% yeast extract were autoclaved and cooled to 30° C. After acidification to pH 5.3 with 10% lactic acid, each was inoculated with 1-2% of a 96 hour old culture of propionibacterium starter. Each propionibacterium starter was grown in sodium lactate broth (see Example 2).

After 96 hours incubation at 30° C., the pH of all cultures was adjusted to 6.0 with 10% sodium hydroxide, followed by pasteurization. Samples of each were then assayed against six different gram negative bacteria using a Well Assay Standard Procedure (see Example 5).

The following tables represent inhibitory activity (expressed as the diameter of the zone of inhibition as measured in mm) of the metabolites of ten different propionibacteria assayed against six different gram negative bacteria. Potassium sorbate (10%) and uninoculated skim milk were used as controls.

TABLE I

INHIBITORY ACTIVITY OF *PROPIONIBACTERIA METABOLITES* AFTER 4 DAYS OF INCUBATION

| | PROPIONIBACTERIA | | Gram Negative Food Spoilage Bacteria | | | | | |
|---|---|---|---|---|---|---|---|---|
| NUMBER | SPECIES DESIGNATION | STAIN NUMBER | Ps. putida | Ps. fluorescens | Ps. aeruginosa | Ps. maltophilia | Ent. cloacae | E. coli |
| $P_1$ (ISU) | P. freudenreichii subsp. shermanii | $F_{24}$ | 10 | 13 | 11 | 0 | <u>10</u> | <u>12.5</u> |
| $P_7$ (ISU) | P. freudenreichii subsp. shermanii | 52 | <u>10</u> | 10 | <u>11</u> | 0 | 0 | 0 |
| $P_{12}$ (ISU) | P. freudenreichii subsp. shermanii | 58 | <u>10</u> | 11 | <u>11</u>.5 | 9 | 0 | 0 |
| $P_{15}$ (ISU) | P. thoenii | TH20 | 13 | 13 | 14 | 18 | <u>10</u> | <u>14</u> |
| $P_{25}$ (ISU) | P. jensenii | J17 | 0 | 0 | 0 | 0 | 0 | 0 |
| $P_{31c}$ (ATCC) | P. shermanii | | 19 | 25 | 17.5 | 19 | 21 | 24 |
| 4874 (ATCC) | P. thoenii | | 0 | 0 | 0 | 0 | 0 | 0 |
| 4869 (ATCC) | P. jensenii | | 0 | 0 | 0 | 0 | 0 | 0 |
| 6207 (ATCC) | P. freudenreichii | | 0 | 0 | 0 | 0 | 0 | 0 |
| 9616 (ATCC) | P. shermanii | | 13 | 13 | 14 | 0 | 0 | <u>14</u> |
| Control | | | 0 | 0 | 0 | 0 | 0 | 0 |
| Sorbate | | | 12 | 12.5 | 10 | 30 | 18 | — |
| *8262 (ATCC) | P. shermanii | | 14 | <u>14</u> | 14 | — | 0 | 0 |
| *9615 (ATCC) | P. shermanii | | 13 | <u>15</u> | 16 | — | 0 | 0 |
| *9617 (ATCC) | P. shermanii | | 15 | <u>14</u> | 14 | — | 0 | 0 |
| *13673 (ATCC) | P. shermanii | | 14 | <u>14</u> | 15 | — | 0 | 0 |
| *Control | | | 0 | 0 | 0 | — | 0 | 0 |
| *Sorbate | | | 17 | 16 | 14 | — | 28 | 35 |

Note:
Underlined numbers indicate a very hazy zone
ISU is the number for cultures obtained from Iowa State University, Department of Food Technology, Propionibacteria Culture Collection.
ATCC is the American Type Culture Collection Number. The well size is 6 mm in diameter and the total diameter of inhibition including the well is measured, except when there is no inhibition observed. Thus, a number of 10 means the well plus the inhibition zone is 10 mm while a 0 means no inhibition around the 6 mm well.
For the gram negative food spoilage bacteria, Ps. represents *Pseudomonas*.
*The last six sets of data were collected on a different day than the other data in this table.
— Not done.

TABLE II

INHIBITORY ACTIVITY OF *PROPIONIBACTERIA METABOLITES* AFTER 7 DAYS OF INCUBATION

| | PROPIONIBACTERIA | | Gram Negative Food Spoilage Bacteria | | | | | |
|---|---|---|---|---|---|---|---|---|
| NUMBER | SPECIES DESIGNATION | STAIN NUMBER | Ps. putida | Ps. fluorescens | Ps. aeruginosa | Ps. maltophilia | Ent. cloacae | E. coli |
| $P_1$ (ISU) | P. freudenreichii subsp. shermanii | $F_{24}$ | 13 | 12 | 12 | 27 | 0 | 0 |
| $P_7$ (ISU) | P. freudenreichii subsp. shermanii | 52 | 13 | 14 | 14 | 16 | 0 | <u>13</u> |
| $P_{12}$ (ISU) | P. freudenreichii subsp. shermanii | 58 | 14 | 14 | 14 | 0 | 0 | 15 |
| $P_{15}$ (ISU) | P. thoenii | TH20 | 13 | <u>15</u> | 13 | 0 | 0 | 0 |

TABLE II-continued

INHIBITORY ACTIVITY OF *PROPIONIBACTERIA METABOLITES* AFTER 7 DAYS OF INCUBATION

| | PROPIONIBACTERIA | | Gram Negative Food Spoilage Bacteria | | | | | |
|---|---|---|---|---|---|---|---|---|
| NUMBER | SPECIES DESIGNATION | STAIN NUMBER | Ps. putida | Ps. fluorescens | Ps. aeruginosa | Ps. maltophilia | Ent. cloacae | E. coli |
| P25 (ISU) | P. jensenii | J17 | 0 | 0 | 0 | 0 | 0 | 0 |
| P31c (ATCC) | P. shermanii | | 13.5 | 12 | 14 | 0 | 0 | 0 |
| 4874 (ATCC) | P. thoenii | | 0 | 0 | 0 | 0 | 0 | 0 |
| 4869 (ATCC) | P. jensenii | | 0 | 0 | 0 | 0 | 0 | 0 |
| 6207 (ATCC) | P. freudenreichii | | 0 | 0 | 0 | 0 | 0 | 0 |
| 9616 (ATCC) | P. shermanii | | 13 | 11 | 13.5 | 0 | 0 | <u>14</u> |
| Control | | | 0 | 0 | 0 | 0 | 0 | 0 |
| Sorbate | | | 12 | 14 | 11 | 35 | 18 | 25 |

Note:
Underlined numbers indicate a very hazy zone
ISU is the number for cultures obtained from Iowa State University, Department of Food Technology, Propionibacteria Culture Collection.
ATCC is the American Type Culture Collection Number. The well size is 6 mm in diameter and the total diameter of inhibition including the well is measured, except when there is no inhibition observed. Thus, a number of 10 means the well plus the inhibition zone is 10 mm while a 0 means no inhibition around the 6 mm well.
For the gram negative food spoilage bacteria, Ps. represents Pseudomonas.

Data in the tables show that all of the gram negative microorganisms tested were inhibited by at least one species of Propionibacteria. The potassium sorbate control required a 10% solution to show effects comparable to the metabolites of propionibacteria. This is a dramatic finding as sorbates are commonly used as food preservatives but are only used in concentrations of about 0.1% or 100 times less than required in these controls. Data also show that the activity is related to incubation time in some cases (compare 4 days of incubation data to 7 days of incubation data). Of course, it is relatively easy to optimize incubation time. The inhibition is due to some metabolite or metabolites other than propionic acid (see Examples 2, 5 and 6-8). Further, data in the tables show that propionibacteria metabolite inhibition of gram negative microorganisms is variable within Propionibacteria species and subspecies or strains. This has not previously been known because it has not even been previously known that such inhibition of gram negative microorganisms occurs. Now that such an effect is known, it is relatively easy to "screen" species of propionibacteria to identify those which produce a metabolite or metabolites as disclosed herein.

EXAMPLE 2

It is now discovered that propionibacteria metabolites can be incorporated into cottage cheese to inhibit undesirable spoilage microorganisms. The bacteria can be produced separately from the cottage cheese and concentrated after growth and prior to utilization or just grown to high numbers and then added to the cottage cheese "cream". Alternatively, the cottage cheese "cream" can be cultured with the propionibacteria prior to creaming. Or propionibacteria can be added during creaming and allowed to produce metabolites during storage of the cottage cheese. Further, the propionibacteria can be used along with usual cultures to "set" the cottage cheese from the beginning of the cottage cheese manufacture.

Flasks (100-ml capacity containing magnetic stirrer bars) of nonfat milk containing 0.1% yeast extract were pasteurized at 85° C. for 45 minutes. They were cooled to 30° C. and acidified to pH 5.3 with 10% lactic acid. *Propionibacterium shermanii* (ATCC Strain 9616) was added at the rate of 1% from a 48-hour old culture grown up in sodium lactate broth (Tripticase, 10.0 g; yeast extract, 10.0 g; 60 percent sodium lactate solution, 16.7 ml; monopotassium phosphate, 0.25 g; manganous sulfate, 0.005 g or 0.5 ml of a 0.1 M solution; and water, 1000 ml; pH-7.0 before autoclaving at 121° C. for 15 minutes) at 30° C. Flasks were placed on a six station magnetic stirrer and slowly agitated during the entire incubation period.

A control flask uninoculated with the propionibacteria was similarly treated. Samples were taken at 24, 48, 72 and 96 hours and assayed for acetic and propionic acids using a Model 5710A Hewlett Packard gas chromatograph equipped with a Model 3380A integrator. Samples were also tested for inhibitory activity against a psychrotropic gram negative, slime-producing cottage cheese spoilage organism supplied by H. P. Hood, Inc., 56 Roland St., Boston, Mass. This preparation was found by electron microscopy to contain Pseudomonas (monitrichous flagella) cells. These organisms are important cottage cheese spoilage bacteria (Dr. Paul Swensen, H. P. Hood, Inc., personal communication) and are now maintained in and available from the Department of Microbiology at Oregon State University; the bacterium was identified as *Pseudomonas putida*.

The test for inhibition against this spoilage bacterium was carried out by adding 1%, 2%, 3%, 4%, 5% and 10% (v/v) amounts of autoclaved (121° C. for 15 minutes) *P. shermanii* 9616 milk culture taken at the various time intervals of growth (and autoclaving as obtained or neutralizing to pH 7.0 with calcium hydroxide prior to autoclaving) to 100 ml of crystal violet tetrazolium agar (CVT agar—Tryptone 5.0 g; yeast extract, 2.5 g; glucose, 1.0 g; distilled water, 1000 ml; agar, 15.0 g; adjust to pH 7.1; after autoclaving at 121° C. for 15 minutes, add filter-sterilized crystal violet at 0.001 g per liter and 2, 3, 5, triphenyltetrazolium chloride at 0.05 g per liter). Each lot of medium containing the various concentrations of the autoclaved milk culture was then acidified to pH 5.3 with sterile 10% tartaric acid. Several dilutions of an overnight lactose broth (beef extract, 3.0 g; peptone, 5.0 g; lactose, 5.0 g; distilled water, 1000 ml;

pH 6.8-7.0) culture of the psychrotrophic spoilage organism were then made and 1.0 ml aliquots added to sterile petri plates. About 10 to 15 ml of CVT agar then was added and the plates incubated at room temperature (25° C.) for 48 hours. On this medium the psychrotrophic spoilage organism grew as large, (1 to 5 mm diameter) deep red, glistening colonies. The amount of inhibition in comparison to control plates containing no autoclaved P. shermanii culture could then be calculated as follows for each concentration of culture taken at the different time intervals:

percent inhibition =

$$\frac{\text{Colonies on Control} - \text{Colonies on Test Plate}}{\text{Colonies on Control}} \times 100$$

Results obtained in analyzing the neutralized (pH 7.0) samples for acetic acid and propionic acids were as follows:

TABLE III

| Hours | mg/l (ppm) | |
|---|---|---|
| | Acetic Acid | Propionic Acid |
| 24 | 869 | 774 |
| 48 | 439 | 556 |
| 96 | 767 | 706 |

Essentially the same data were obtained for unneutralized samples.

In analyzing the samples for inhibition of the psychrotrophic, slime-producing cottage cheese spoilage organism, the following results were obtained:

TABLE IV

Percent inhibition of cottage cheese spoilage organism by various amounts of P. shermanii 9616 milk culture grown in pasteurized* milk.

| Culture Added (Percent) | Time Sampled (hours) | | | |
|---|---|---|---|---|
| | 24 | 48 | 72 | 96 |
| 0 | 0 | 0 | 0 | 0 |
| 1 | 62 | 50 | 100 | 96 |
| 2 | 56 | 100 | 100 | 90 |
| 3 | 42 | 100 | 44 | 97 |
| 4 | 88 | 100 | 46 | 98 |
| 5 | 96 | 100 | 52 | 97 |
| 10 | 50 | 100 | 36 | 97 |

*Milk pasteurized at 85° C. for 45 minutes and then acidified with lactic acid to pH 5.3.

In another experiment, the Propionibacterium shermanii 9616 culture was grown under the same conditions in nonfat milk except the milk was autoclaved and not acidified to pH 5.3 with lactic acid. This was done because microscopic examination of the culture grown in the pasteurized (85° Cm 45 minutes) nonfat milk revealed sporeformers emerging by 48-72 hours. In fact, the counts of heat tolerant forms (survive 60° C. for 30 minutes) at zero time and at 72 hours were 100 per ml and $10^7$ per ml, respectively. It was felt this might confound interpretation of the data in the pasteurized samples. The following data were obtained with the autoclaved milk grown cultures.

TABLE VII

| Hours | mg/l (ppm) | |
|---|---|---|
| | Acetic Acid | Propionic Acid |
| 24 | 310 | 106 |
| 48 | 87 | 35 |
| 72 | 582 | 713 |

TABLE VII-continued

| Hours | mg/l (ppm) | |
|---|---|---|
| | Acetic Acid | Propionic Acid |
| 96 | 788 | 1064 |

In this case, we see the maximum acetate and propionate production delayed until at least 96 hours in contrast to the cultures which were acidified with lactic acid to pH 5.3. This biological difference may be due to the fact that acetate and propionate are produced from lactate which the propionibacteria did not need to produce in the acidified samples but which they produced gradually in the nonacidified samples. An exact understanding of growth or metabolism variations is not required Data on inhibition of the cottage cheese spoilage organism are in the following table.

TABLE VIII

Percent inhibition of cottage cheese spoilage organism by various amounts of P. shermanii culture grown in autoclaved* milk.

| Culture Added (percent) | Time Sampled (hours) | | |
|---|---|---|---|
| | 24 | 48 | 96 |
| 0 | 0 | 0 | 0 |
| 1 | 36 | 90 | 71 |
| 2 | 44 | — | 84 |
| 3 | 44 | 97 | 90 |
| 4 | 66 | — | 91 |
| 5 | 100 | 90 | 93 |
| 10 | 100 | 98 | 92 |

*Milk autoclaved 15 minutes at 121° C.

If one considers that propionic and acetic acids may be solely responsible for the inhibition seen, the time at which these acids are maximally produced should agree with the times at which samples show maximum inhibition of the spoilage bacteria. This, however, is not the case. In the case of the pasteurized, acidified growth culture, maximum acetate and propionate occurred by 24 hours but maximum inhibition not until at least 48 hours. In case of the autoclaved, nonacidified milk, maximum acetate and propionate occurred at 96 hours but maximum inhibition of spoilage bacteria at 24 to 48 hours. Further, these data show that metabolites added to provide as little as 0.001 percent added propionate provided some inhibition of the psychrotrophs. These data show that propionibacteria produce a metabolite or metabolites other than propionic acid which, in unconcentrated form, have an inhibitory effect on gram negative psychrotrophic bacteria which is surprising since Meade and Stringham (U.S. Pat. No. 2,465,905) and Sherman (U.S. Pat. No. 1,937,672) teach that the metabolites of propionibacteria are not inhibitory to bacteria. In concentrated form the metabolites are even more inhibitory. These data also show that propionibacteria produce at least one metabolite other than propionic acid which has an inhibitory effect on gram negative psychrotrophic bacterial food spoilage microorganisms and the material can be provided in a food product in an amount sufficient to inhibit the spoilage organism. These data further show the preservation of a food product with a propionibacterial fermented medium that contains insufficient propionic acid to preserve the food product.

EXAMPLE 3

*Propionibacterium shermanii* (ATCC Strain 9617 was grown in a sodium lactate broth (Example 2) for 48 hours. Five hundred gallons of skim milk were then pasteurized at 190° F. for 45 minutes, and subsequently cooled to 86° F. The cooled milk was acidified using 85 percent reagent grade lactic acid to a pH of 5.3 and then inoculated with 0.5% of the *Propionibacterium shermanii* culture. The inoculated milk was slowly agitated during incubation for 48 hours, and thereafter neutralized with sodium hydroxide to pH 7.0. The neutralized liquid was pasteurized at 145° F. for 20 minutes, cooled to ambient temperature (about 75° F.), pumped through sterile lines into six-gallon sterile plastic bags and then frozen.

When thawed, the liquid medium was very active in inhibiting the growth of the psychrotropic gram negative, slime-producing cottage cheese organism mentioned in Example 2.

EXAMPLE 4

220 gallons of milk fortified with 0.1 percent yeast extract were heat-treated at 85° C. for 45 minutes and then cooled rapidly to 30° C. 86 percent lactic acid (Sigma Grade) was then added with agitation until the pH was lowered to 5.3. The milk was then inoculated with a mature culture of 1.25% *Propionibacterium shermanii* (ATCC 9617) and the culture allowed to grow for 48 hours. The final mature growth mixture (bacterial soup) was adjusted close to neutrality with NaOH, pasteurized, a portion retained as a liquid, and the remainder spray-dried using a commercial box-type spray dryer. The liquid and spray dried powders were incorporated into cottage cheese dressing with slime producing bacteria to evaluate their effect on the keeping quality of the final creamed cottage cheese. The dressing was formulated at the upper level of inhibitor (liquid or spray dried bacterial soup mixture) addition to be tested, and lower levels were obtained by backblending at specified ratios with a control dressing. The final inhibitor addition level was calculated to be the percent of inhibitor on a solids basis per pound of finished cottage cheese.

A control cottage cheese was made along with all testing variables. Initially, in order to establish an effective but not excessive addition level of the inhibitor and also a reasonable inoculation level of the surface slime organism, various samples were evaluated with different inhibitor addition and inoculation levels. The slime inoculant was mixed in the cottage cheese at specified counts per pound of cheese. Control and inhibitor samples, both inoculated and noninoculated, were packed and sealed with heat sealed foil lids. Samples were set in storage for evaluation at 45° and 50° F.

Evaluations indicated a positive inhibitory effect of the spray-dried powder in test sample versus control in that the storage time at 45° and 50° F. was increased 7 to 10 days before surface slime growth appeared. Results with liquid which had 8.8% solids were similar. The percent inhibitor in the finished product was 0.00% (control) 0.12%, 0.24%, 0.36% and 0.48%. All samples were inoculated with spoilage bacteria at 2000/lb or 8000/lb along with a noninoculated set of each inhibitor level as a control. Results showing the number of days before surface slime growth appeared in samples from a 4000 lb batch of cottage cheese are summarized in Table IX:

TABLE IX

| Days at 50° F. When Spoilage Appeared | Sample | Inoculation Level of Spoilage Bacteria |
|---|---|---|
| 16 | Control | 8000/lb |
| 23 | Control | 2000/lb |
| 23 | 0.12% Inhibitor | 8000/lb |
| 44 | Control | Noninoculated |
| 56 | 0.12% Inhibitor | 2000/lb |

Flavor evaluations indicate that all noninoculated inhibitor-containing samples were acceptable after 44 days at 50° F. Thus, the inhibitor extended significantly the number of days at 50° F. before surface slime growth appeared.

Further testing of these products was carried out in cottage cheese as above with the following conditions:
  (a) Control—No inhibitor added.
  (b) Spray dried inhibitor addition—0.30% level.
  (c) Spray dried inhibitor addition—reconstituted and pasteurized at 255° F.—36 sec.—0.30% level.
  (d) Skim based liquid—14.50% solids—0.15% level.

Condition (c) was set up to safeguard against possible microbial contamination by the inhibitor powder. Condition (d) was included to compare the inhibitory activity of the liquid product versus the spray dried sample.

The following table shows results of these tests where the number of days before the appearance of spoilage slime is given:

TABLE X

| Days When Spoilage Appeared | Conditions |
|---|---|
| 6 days | Control - Inoculated |
| 14 days | Condition (b) - Inoculated - 1 of 9 samples |
| 17 days | Condition (b) - 100 percent Condition (c) - 100 percent |

From these observations it is clear that the spray dried material produced in this example also displays inhibitory activity.

Once again, it is shown that propionibacteria produce metabolites which are inhibitory to gram negative slime producing bacteria.

EXAMPLE 5

Partial Characterization of Metabolites of Propionibacteria Affecting Inhibitor Growth The molecular weight of a microbial inhibitor produced by propionibacteria was estimated using Bio-Gel P4 (Bio-Rad) gel filtration which separates molecules based on their molecular weights compared to known molecular weight standards.

A sample of propionibacteria metabolites produced in dextrose broth by growing propionibacteria 9616 for four days was mixed with standards of known molecular weight and applied to the column. Each fraction collected was assayed for inhibition of gram negative psychrotropic bacterial growth using a standard well assay (procedure shown below).

Of over 100 fractions collected, anti-microbial activity was only detected in samples 21 to 25. The peak fraction of activity corresponds to a molecular weight of approximately 1,000. No activity whatsoever was detected in fractions corresponding to the molecular weight of propionic acid (MW 74.1), i.e. fractions 90 to 98 (not shown). Virtually 100% of the activity applied to the column was recovered in the active fractions.

Clearly the most active propionibacterial metabolite responsible for inhibiting gram negative growth is not propionic acid. These data show that at least one metabolite other than propionic acid has an inhibitory effect on gram negative bacteria. The column data are not exclusive in that the highest molecular weight control was Vitamin B-12, molecular weight 1,350. Other metabolites may certainly exist with molecular weights other than about 1,000 which are not propionic acid and which do inhibit microorganisms. In fact, some preliminary research using electrophoresis gels suggest a substance with molecular weight about 13,000 is produced by propionibacteria which is inhibitory to gram negative microorganisms. These types of experiments do not allow determination of exact quantities of active metabolites. Thus, it is not currently possible to refer to concentrations or amounts of the purified metabolites which would be effective. However, the scope of this invention includes such purified metabolites. Thus, we disclose that microorganism inhibitors of molecular weight greater than a few hundred (and certainly greater than propionic acid) are produced by propionibacteria, which has not previously been known. These new metabolites are referred to herein as metabolites of molecular weight greater than 300 which have antimicrobial activity. These substances will have a variety of uses as inhibitors of gram negative bacteria. For example, Pseudomonas is greatly inhibited by the newly discovered active metabolites and Pseudomonas present a dire medical problem for treatment, especially in burn patients and some systemic infections. The newly discovered nonpropionic acid metabolite(s) of propionibacteria can be isolated, purified and utilized, in purified or semi-purified form, to inhibit such gram negative bacteria.

Additional evidence that there is a propionibacterial metabolite responsible for yeast inhibition which is not propionic acid is shown by the data below (Table XI) demonstrating that no correlation exists between propionic acid concentrations and yeast inhibition. In this experiment, two lots of inhibitor prepared as in Example 3 were found to have significantly different propionic acid concentrations. However each were shown to be equally effective in inhibiting yeast growth (assay procedure below).

As a control, skim milk with added propionic acid was assayed for its inhibitory nature against yeast in an identical fashion. No inhibition was detected at any level of propionic acid tested, confirming that propionic acid is not the yeast inhibitor in propionibacteria metabolites. Data in Table XI below clearly show that 0.02% propionic acid does not inhibit yeasts as is expected from the work of Wolford and Anderson In fact, they teach that 2% propionic acid would be needed.

These data show a very new and unexpected use for propionibacteria metabolites which has previously not been recognized or used in this fashion. They show that certain propionibacteria produce at least one metabolite other than propionic acid, which has a molecular weight greater than 300, and has an inhibitory effect on a food spoilage yeast, and that a material containing the metabolite can be provided in a food product normally devoid of propionibacteria in an amount sufficient for the metabolite to inhibit the yeast. They further show that said inhibition can occur when there is insufficient propionic acid present to inhibit the yeast. They also show that a propionic acid bacteria fermented material can comprise one or more metabolites other than propionic acid such that the material has a greater inhibitory effect than could be caused by its propionic acid content.

TABLE XI

PERCENT INHIBITION OF YEAST GROWN IN THE PRESENCE OF INHIBITOR

| Control Colonies: % Inhibitor* | | 800 | 78 | 8 | % Propionic Acid in Final |
|---|---|---|---|---|---|
| | | | % Inhibition | | |
| Mixture | | | | | |
| LOT NO. 023 | 1 | 25 | 50 | 100 | .0023 |
| | 5 | 75 | 100 | 100 | .0165 |
| | 10 | 100 | 100 | 100 | .0230 |
| LOT NO. 343 | 1 | 25 | 50 | 100 | .0002 |
| | 5 | 50 | 75 | 100 | .0010 |
| | 10 | 100 | 100 | 100 | .0020 |

PERCENT INHIBITION OF YEAST GROWN IN THE PRESENCE OF SKIM MILK PLUS PROPIONIC ACID

| Control Colonies: % Additive* | | 2000 | 187 | 25 | % Propionic Acid in Final Mixture |
|---|---|---|---|---|---|
| | | | % Inhibition | | |
| SKIM PLUS | 1 | 0 | 0 | 0 | .0023 |
| 243 ppm | 5 | 0 | 0 | 0 | .0165 |
| Propionic Acid | 10 | 0 | 0 | 0 | .0230 |
| SKIM PLUS | 1 | 0 | 0 | 0 | .0002 |
| 2270 ppm | 5 | 0 | 0 | 0 | .0010 |
| Propionic Acid | 10 | 0 | 0 | 0 | .0020 |

LOT NO. 023 2,270 ppm propionic acid (0.227%)
LOT NO. 343 243 ppm propionic acid (0.024%)
*Percent of propionibacterial metabolites added to potato dextrose agar (PDA) containing yeast (See Yeast Assay which follows).
**Percent of additive (which was skim milk containing added propionic acid) added to potato dextrose agar (PDA) containing yeast.

These data show that a propionibacteria inhibitor product made according to the present invention can inhibit yeast even though it contains as little as 1/10,000th the amount of propionic acid that Wolford says is the minimum necessary to inhibit yeast. Propionibacteria fermented material inhibits yeast, but the amount of propionic acid that is in the material is not inhibitory to yeast. Such a material would not be expected to inhibit yeast based on propionic acid content since Wolford et al. teach that 2%–3% propionic acid is needed to inhibit yeast.

Different strains of propionibacteria may produce variable amounts of propionic acid and variable amounts of the newly discovered anti-yeast metabolites. Now that it is disclosed that propionibacteria can produce such anti-yeast metabolites, it is a simple matter for one skilled in the art to "screen" propionibacteria for their ability to produce inhibitors to yeasts. "Successful" strains may produce either small amounts or relatively large amounts of propionic acid. This is very different from the teachings of Anderson where only one specific strain of propionibacteria is employed because it produces large amounts of propionic acid and because Anderson observes the desired activity (mold inhibition) as being directly proportional to the amount of propionic acid produced by his specific strain. The present invention differs further from any previous teachings as it is now revealed that there are metabolites of propionibacteria, other than propionic acid, which inhibit yeasts, mold and bacteria. Efforts were taken to determine whether the metabolite responsible for inhibiting the growth of gram negative bacteria was amino acid or polypeptide or protein in nature. Samples of Inhibitor were treated with a variety of proteolytic enzymes (see Table XII). As is shown, the action of three of the four enzyme treatments eliminated the antimicrobial activity, suggesting an amino acid or polypeptide or protein nature. It is anticipated that isolation and purification or semi-purification of the active metabolite will find broad usage as an inhibitor of undesirable gram negative microorgamisms.

TABLE XII
EFFECT OF PROTEOLYTIC ENZYMES ON THE INHIBITORY ACTIVITY OF INHIBITOR

| ENZYMES | INHIBITORY ACTIVITY AFTER TREATMENT |
|---|---|
| Protease (papaya) | − |
| - Chymotrypsin | − |
| Pepsin | − |
| Trypsin | + |

1% Inhibitor (prepared as in Example 3) was treated with each enzyme at a concentration of 0.1% w/v and at the optimal pH for each. After standard incubation, the enzymes were inactivated by heat, the pH adjusted and the samples assayed against P. putida. Since the agent(s) responsible for the unexpected activity of propionibacteria metabolites is an unknown substance(s), the purpose of this enzyme treatment was to determine whether an amino acid or polypeptide or protein type material was involved in inhibiting the growth of gram negative psychrotrophic bacteria. Enzymatically untreated Inhibitor was used as a control.

WELL ASSAY STANDARD PROCEDURE

The purpose of a well assay in microbiology is to evaluate inhibition or stimulation of an organism by the test material. If a clear zone develops around the well due to lack of bacterial growth then inhibition occurred, and the larger the zone the greater the inhibition. If growth around the well is more luxuriant than elsewhere, then stimulation of bacterial growth occurred. This assay is used in examples 1, 2, and 5.

Medium Used—CVT agar that has been adjusted to pH 5.3, 17 ml per plate. (See procedure below for CVT composition). Plates should be made at least 48 hours before use.

Lawn—Use an appropriate gram negative organism e.g. P. putida. Grow culture overnight (24 hrs) in lactose broth at 30° C.

Dilute with sterile peptone water about 1:10-1:100 until a reading of 90% transmittance is obtained at 595 nm. Add 2 drops from a 1.0 ml pipet of above solution and spread on one of the plates. When lawn has "dried", cut and remove wells. Add 2 drops test liquid per well and incubate overnight.

CVT agar (per liter of water add 5 g tryptone, 2.5 g yeast extract, 1.0 g glucose, 1.0 ml of a 0.1% solution of crystal violet in ethanol solution, and 15.0 g agar, adjust pH to 7.1) is mixed, placed in a steamer until melted, pour in 100 ml volumes in dilution bottles, and autoclave for 15 minutes at 121° C. After autoclaving, the bottles of CVT agar were placed in a 46° water bath. After the agar was cooled, each bottle had added 0.4 ml of a 10% sterile solution of tartaric acid in water and 1.0 ml of a filter sterilized 1.0% solution of 2, 3, 5–1.0 ml of a filter sterilized 1.0% solution of 2, 3, 5-triphenyl -2H - tetrazolium chloride (INT) in water. The pH should be 5.3.

YEAST ASSAY AND INHIBITOR

An assay against yeast was conducted using potato dextrose agar (PDA), acidified to pH 4.0 and supplemented with INT to distinguish colonies from debris. Colonies on the plate will eventually "catch up" to the controls. As a result, the colonies are incubated at room temperature for two days and then read. There should be a significant size difference (indicating fewer numbers of cells) between Inhibitor and control plates.

INT is p-Iodonitrotetrazolium Violet and is obtained from Sigma Chemical (Cat. #I-8377). It is prepared as a 0.29% solution in water and filter sterilized. Do not autoclave. INT is used at a level of 0.5 ml per 100 ml of melted and cooled agar. Colonies growing in the presence of INT will take on a red color.

EXAMPLE 6

Skim milk was fermented with Propionibacterium shermanii (ATCC Strain 9616) with some agitation to prevent development of large cheese curds. The resulting composition, including all the bacterial metabolites, was freeze-dried. Fifteen grams of freeze-dried composition were added to 85 ml of water and acidified with hydrochloric acid to a pH of 4.6. This reconstituted mixture was then centrifuged at 10,000 rpm for 20 min at 4° C., and the supernatant sterilized by passing it through a 0.22 filter. The clarified supernatant fraction was then applied to a Sephadex G-25 column that was previously equilibrated with 0.2M sodium chloride to control viscosity and contamination. The flow rate of the column was 7.5 ml per hour.

Each fraction of the column was assayed for inhibitory activity by way of a plate assay. Crystal violet tetrazolium agar, acidified to pH 5.3, is selective for gram negative organisms and was used for the assay. One ml samples of serial dilutions of overnight cultures of psychrotrophic gram negative spoilage organisms isolated from cottage cheese were mixed with CVT agar that contained various levels of the fraction to be tested.

Inhibitory properties of 70 fractions collected from the G-25 column varied from fraction to fraction, but it is clear that some fractions with molecular weights much different than propionic acid had substantial inhibiting properties. Ten separate fractions showed major inhibitory properties (100 percent inhibition of $10^4$ dilution of organisms) while several other fractions had lesser activity (100 percent inhibition of $10^6$ dilution of organisms). Since the fractions should represent different molecular weight ranges and any propionic acid (molecular weight=74.08) should be contained only in the first few fractions, it is concluded that at least part of the microbial inhibitory activity is due to something other than just the propionic acid present and the unknown substance(s) have a molecular weight greater than 300. This experiment shows that the unique materials described herein can be separated by densities and by molecular weight and can be concentrated by freeze drying.

EXAMPLE 7

The relative activity of different preparations of propionibacteria cultured skim milk, each prepared as in Example 11 to inhibit gram negative psychrotropic bacteria is defined as the percent of composition needed to completely inhibit the growth of 250–700 colonies as measured in the plate assay technique of Example 6. As a result, the greater the percent of metabolite needed (or the greater the relative activity), the less effective is the inhibition of gram negative organisms.

Data in Table XIII show that there is a variable relationship between the propionic acid levels, as measured by gas chromatography, and the relative activity of the metabolite composition, when measured by the plate assay.

TABLE XIII

| Sample Number | Analysis of Samples Propionic Acid (ppm) | Relative Activity |
| --- | --- | --- |
| 1 | 1819 | 0.50% |
| 2 | 1698 | 1.00% |
| 3 | 3932 | 0.50% |
| 4 | 2687 | 1.00% |
| 5 | 2752 | 2.00% |
| 6 | 3585 | 2.00% |
| 7 | 4130 | 2.00% |
| 8 | 5510 | 1.00% |
| 9 | 4950 | 1.00% |
| 10 | 4500 | 0.50% |
| 11 | 6650 | 0.25% |
| 12 | 4700 | 0.50% |
| 13 | 5100 | 0.50% |
| 14 | 6950 | 0.50% |
| 15 | 5550 | 0.25% |
| 16 | 7358 | 1.00% |
| 17 | 11870 | 0.50% |
| 18 | 8745 | 0.25% |
| 19 | 9876 | 0.50% |

Sample number 1 containing 1,819 ppm propionic acid had a relative activity of 0.50%, indicating that it took 0.50% of the metabolite composition to inhibit the growth of 250-700 colonies. Sample number 17 had 11,870 ppm propionic acid (6.5 times the amount of sample), but still had a relative activity of 0.50%.

In a similar fashion, sample number 8 contained 5,510 ppm propionic acid and had a relative activity of 1.0%, whereas sample 15 with an almost identical propionic acid level (5,550 ppm) had a relative activity of 0.25%—four times the activity. These results confirm the finding that this invention is not solely dependent on propionic acid concentration, in contrast to the teaching of Anderson. For this invention, there may be a relatively large amount or relatively small amount of propionic acid and the metabolite mixture is still effective to preserve foods. The main value of considering propionic acid concentration is to differentiate this invention from prior art; that is, to explain the uniqueness. These data show the use of a food preservative additive comprising a mixture of metabolites of propionibacteria, including inhibitory metabolites other than propionic acid, which mixture is more inhibitory to gram negative psychrotrophs than a weight of pure propionic acid which is equal to the pure propionic acid content of the mixture.

EXAMPLE 8

Comparisons of tests were made to determine the relative effects of a product prepared as in Example 11 on four gram negative spoilage organisms in half and half.

Two quarts of half and half (50 percent cream and 50 percent milk, 18 percent milk fat) were combined in a sterile beaker and acidified to pH 5.3 with lactic acid. The mixture was then dispensed with a sterile graduated cylinder in 125 ml volumes into 13 sterile 250 ml Belco culture flasks with snug fitting metal closures. Four pairs of flasks were treated in the following manner. One flask of the pair was inoculated with one ml of a $10^{-8}$ dilution of an overnight lactose broth (Difco) culture of a gram negative spoilage organism isolated from cottage cheese (organism A). This flask is called the control. One flask from this pair then had added 1.25 ml of the liquid metabolite propionibacteria mixture to give a 1.0 percent concentration of the liquid metabolite mixture, and the same amount of spoilage organisms added. This same procedure was followed for the other three pairs of flasks using different organisms "B", "C", and "D", also gram negative spoilage organisms isolated from cottage cheese and important to keeping quality. Another flask had no organisms or metabolites added and served as an indicator of background contamination levels.

The flasks were kept at 45° F. and plated at 1, 4, 6, 8, and 12 day intervals in CVT agar. CVT agar is made by adding 23.5 grams of Plate Count Agar (Difco) to one liter of distilled water. Also, add 1.0 ml of a solution of 0.1 gram crystal violet (Difco) in 100 ml ethanol (Sigma). Autoclave, cool, and immediately before pouring plates add 5.0 ml of a filter sterilized solution of 1.0 gram, 2,3,5-triphenyl-2H-tetrazolium chloride (Sigma) in distilled water. After platting, the plates were incubated at 30° C. for two days and counted. The results of these experiments appear in Table XIV.

TABLE XIV

|  | Day 1 | Day 4 | Day 6 | Day 8 | Day 12 |
| --- | --- | --- | --- | --- | --- |
| Background Flask | <10 | <10 | <10 | <10 | <10 |
| Organism "A" |  |  |  |  |  |
| Control | 50 | 71,000 | 15,000,000 | 160,000,000 | 140,000,000 |
| Metab. Mix | <10 | 380 | 57,000 | 5,800,000 | 6,700,000 |
| Organism "B" |  |  |  |  |  |
| Control | <10 | 3,500 | 750,000 | 90,000,000 | 700,000,000 |
| Metab. Mix | 20 | <10 | <10 | 290 | 330 |
| Organsim "C" |  |  |  |  |  |
| Control | 20 | 29,000 | 12,000,000 | 130,000,000 | 260,000,000 |
| Metab. Mix | 10 | 89 | 140,000 | 3,700,000 | 1,800,000 |
| Organism "D" |  |  |  |  |  |
| Control | 60 | 210,000 | 32,000,000 | 180,000,000 | 3,600,000.000 |
| Metab. Mix | 10 | 640 | 200,000 | 8,400,000 | 32,000,000 |

As can be seen from the plate count numbers for the background flask, manipulation of the half and half introduced no contaminating gram negative organisms. From this, we can say the only gram negative organisms present in the experimental flasks are ones inoculated.

All control flasks showed rapid and prolific growth of the inoculated gram negative organisms. This demonstrates that the spoilage organisms grew readily in half and half and that a pH of 5.3 does not overly inhibit their growth. Any change between the control flasks and the metabolite mixture flasks would be inhibition due to the added substance.

The effect of the metabolite mixture on gram negative organisms is profound. All four organisms from four days to twelve days show a dramatic decrease in cell population with the metabolite mixture as compared to the control. For all data points there was a least about a hundredfold difference compared to the control flasks. These data point to a much greater effect of the metabolite mixture than can be attributed to just the propionic and acetic acids present, which produced concentrations of only about 0.0083% and 0.005%, respectively. This experiment shows the invention is useful for half-and-half cream and is effective against a variety of gram negative psychrotrophs.

EXAMPLE 9

*Listeria monocytogenes* is a gram positive bacterium pathogenic for humans. During one outbreak there were 300 cases of listeriosis and 100 deaths occurred in California. The food involved was Jalisco soft (Mexican-style) cheese manufactured under conditions such that the final cheese allowed considerable growth of the pathogen. The Food and Drug Administration has surveyed many dairy plants and products for this dangerous bacterium. Extensive product recalls were necessary on several occasions. The meat industry now is being scrutinized by public health officials to determine whether or not a health threat may be associated with listeria presence in any meat products. Propionibacterial metabolites as prepared in Example 3 were assayed against *Listeria monocytogenes* ATCC 7644 using brain-heart infusion (BHI) agar. The freeze-dried pathogen was transferred in BHI broth and inoculated at 37° C. overnight. BHI with 1.5% agar was acidified to pH 5.3 with 10% tartaric acid and 1 ml of 2, 3, 5-triphenyltetrazolium chloride (1% solution) was filter sterilized and added just before pouring the plates. Dilutions of the bacteria were made using 0.1% peptone water (from $10^{-2}$ to $10^{-8}$ dilutions were used). Liquid propionibacterial metabolites adjusted to pH 5.30 were incorporated into the medium at 1%, 3% or 5% concentrations. After pouring the plates they were inverted and incubated at 37° C. for about 42 hours. Control plates containing *Listeria monocytogenes* were too numerous to count at dilutions of $10^2$ to $10^{-5}$. They were counted on $10^{-6}$ and $10^{-7}$ plates and found to be about 2 times $10^7$ counts. In the presence of 1%, 3%, or 5% Inhibitor, there was 100% inhibition of all *Listeria monocytogenes* at all dilutions. In a repeat experiment, Inhibitor also inhibited *Listeria monocytogenes* although the effect was somewhat less than in the first experiment.

These findings are incredible. Mature propionibacteria cultures have been used as nutrient growth media to support some gram positive bacteria as indicated by Sherman. It is now discovered that this gram positive bacterial pathogen, *Listeria monocytogenes*, is inhibited by metabolites of a Propionibacterium culture.

EXAMPLE 10

Metabolites of propionibacteria as prepared in Example 9 followed by spray drying are shown to inhibit gas formation by heterofermentative gram positive lactobacilli, a common spoilage organism of refrigerated salad dressings, pasta, prepared meats and other refrigerated foods. No diminution in cell growth was demonstrated which shows that the propionibacteria metabolites are in some unknown way inhibitory to the normal metabolism of the food spoilage bacteria, even under conditions where the bacterial spoilage cells continue to multiply. The mechanism of inhibition need not be known to practice this invention, but probably includes inhibition of enzymes. Inhibition of metabolism is not expected as previously referenced to Meade and Stringham with Sherman or in light of Example 13 herein which teaches the use of propionibacteria metabolite mixtures to grow gram positive bacteria. Data in this example confirm that some gram positive bacteria can grow well in the presence of propionibacteria metabolites mixtures, but these data also show a surprising effect to change metabolism such that there is a decrease in undesirable gas production which is often a major component of food spoilage. The following experiment is characteristic of the inhibition observed.

Syringes were partially filled with culture medium (MRS) that contained dilutions of lactobacilli and propionibacteria metabolites. They were then incubated in an up-right position. After an appropriate time period, gas formed by the lactobacilli will cause the plunger to raise. Table XV shows the volume of gas produced after five days of incubation.

TABLE XV

VOLUME OF GAS PRODUCED (ml) BY *HETEROFERMENTATIVE LACTOBACILLI* BACTERIA IN THE PRESENCE OF DRIED PROPIONIBACTERIA METABOLITES (PM) AT A pH OF 4.5.

| | INITIAL CONCENTRATION OF BACTERIA | | | |
|---|---|---|---|---|
| | 100,000/ml | 10,000/ml | 1,000/ml | 100/ml |
| Control | 5.8 | 2.6 | 1.5 | 0.4 |
| 0.5% PM | 3.7 | 1.0 | 0.6 | 0.4 |
| 1.5% PM | 2.0 | 1.0 | 0.6 | 0.0 |

After five days of incubation, the amounts of gas indicated above were produced in this system and the samples were enumerated for viable bacterial cells. In all instances the counts/ml were approximately 10,000,000/ml. That is, although the sample which originally contained 100 gas producers per ml plus 1.5% PM multiplied to 10,000,000/ml there was no measurable gas production in this system (see Table XV). This experiment demonstrates that propionibacterial metabolites can inhibit metabolism of some bacteria in a manner which is beneficial in the preservation of food. It further shows inhibition of gas production of gram positive bacteria. Still further is shown the use of propionibacterial metabolites to inhibit enzymatic or metabolic production of gases important in spoilage of food by a gram positive bacteria. This inhibition is not suggested by propionic acid as shown throughout this specification since others show that gram positive bacteria grow in the amount of propionic acid produced by propionibacteria, and there is no suggestion of any change in metabolism.

EXAMPLE 11

Skim milk was fermented for four days with *Propionibacterium shermanii* (ATCC Strain 9616) with some agitation to prevent development of large cheese curds. The resulting metabolite mixture was neutralized to pH 6.0 with sodium hydroxide, screened and pasteurized with a HTST system. The resulting metabolite mixture had a concentration of propionic acid of 20,700 ppm, and acetic acid concentration of 13,100 ppm, as determined by gas chromatography.

Two vats of strawberry yogurt were made at a commercial dairy. Prior to pasteurization and setting, the acidified metabolite mixture was added to one vat at a concentration of 1.0%.

Samples taken from the two vats were plated at various times to monitor the growth of spoilage yeast present. Dilutions of each sample were plated with Potato- Dextrose agar (acidified with tartaric acid) using standard pour plate technique. Plates were incubated for 3 days at 30° C., then counted. The results appear in Table XVI.

TABLE XVI

|  | 0 Day | 21 Day | 34 Day |
|---|---|---|---|
| Control | <10 | 23 | 900 |
| Metabolite Mix | <10 | 30 | 10 |

These results, in units of viable yeast per gram of yogurt, show control of spoilage yeast organisms which is not due to the final concentration of propionic acid added to the yogurt which was only 0.02%.

Earlier examples showed inhibition of certain food spoilage bacteria. This example now shows inhibition of one of the most difficult of all to control food spoilage microorganisms, yeast. The yeast is inhibited by some metabolite of propionibacteria other than propionic acid. Thus, reference to propionic acid concentrations does not define the invention but only shows that other metabolites are active. This experiment (and others to follow) shows the preservation of a food product against spoilage yeast comprising use of a propionic acid bacterial fermented material that provides insufficient propionic acid to preserve the food.

These data further show the use of a food preservative additive comprising a mixture of metabolites of propionibacteria which is more inhibitory to yeast than a weight of pure propionic acid which is equal to the pure propionic acid content of the mixture. This finding has not previously been taught.

EXAMPLE 12

Commercial yogurt products typically have a pH of 3.5 to 4.5 and a titratable acidity in the range of 0.9 to 2.0 percent expressed as lactic acid. Most commercial yogurts have a fat content of two to four percent. Yogurt may contain coloring and flavoring ingredients, including artificial and natural fruit flavorings, whole fruit, and fruit syrups. Yogurt, particularly the unflavored variety, has a characteristic flavor and aroma that would be expected to be compromised if large amounts of propionates were added.

It is the expectation of many consumers and a requirement in many countries that yogurt contain viable fermentation microorganisms. Such bacteria are consumed to aid digestion. To retain viable bacteria, yogurt cannot be given a final pasteurization to preserve the product for shipment and storage. Thus, yogurt is particularly susceptible to spoilage microorganisms present at the manufacturing and packaging site. Due to its composition, mold and yeast growth are the most common spoilage problems.

As demonstrated by the following examples, the shelf life of yogurt can be extended greatly, without pasteurization that would harm the fermentation bacteria, by adding certain Propionibacterium to a yogurt batch before fermentation or by adding a Propionibacterium growth mixture according to the present invention, either before or after yogurt fermentation. It was found that addition of the propionibacteria or the growth mixture to a yogurt-making batch had no noticeable detrimental effect on the activity of the fermentation bacteria, although they do inhibit other bacteria as shown elsewhere herein.

A number of examples show the addition to yogurt of a growth mixture wherein Propionibacterium cells have been made not viable. This is expected to be the best commercial procedure. But, the use of a growth mixture with viable Propionibacterium might be advantageous due to continued production of metabolites in the yogurt. In a "Swiss-style" mixed fruit yogurt, gas bubbles formed by $CO_2$ released from Propionibacteria might prove to be a desirable sensory characteristic.

A commercially available homestyle yogurt maker (Salton yogurt maker) was used to produce cups of yogurt. The starter cultures employed were commercially available for the production of yogurt (Chr. Hansen's Laboratories, Milwaukee, Wis.). The culture used was R6. The commercially available frozen culture was thawed and added to milk and allowed to mature prior to use. Then 1 ml of this culture was added to 200 ml of 2 percent milk and the yogurt making instructions followed. Excellent yogurt was produced which had a good body, and was a uniform product with a final pH of 4.2. In a separate yogurt preparation, the inoculum consisted of ½ ml of commercially available Hansen's culture combined with 3 ml of Propionibacterium culture. An excellent yogurt was also produced with good body and a final pH of 3.9. In addition, yogurt was prepared by mixing ½ ml of Hansen's culture with 3 ml of Propionibacterium in 200 ml of 2 percent milk which had been fortified with 9 g of nonfat dry milk. The final pH was 3.98 and an excellent, uniform body yogurt was produced. Thus, the presence of the Propionibacterium did not inhibit the production of yogurt in any way. This is quite important since Propionibacterium are known to produce carbon dioxide which might disrupt yogurt formation, but this was not observed. A combination of lactobacillus and propionibacteria has been reported to increase carbon dioxide production ("Stimulating Effect of Lactobacilli on the Growth of Propionibacteria in Cheese," F.F.J. Nieuwenhof, J. Standhouders and G. Hup, Neth. Milk Dairy J. 23, p. 287–239, 1969). This example demonstrated that viable propionibacteria can be used in the production of yogurt to generate their metabolites in the yogurt.

EXAMPLE 13

In this example, yogurt was prepared by inoculating pasteurized 6.25 percent nonfat dry milk in water with Propionibacterium, waiting 12 hours and then inoculating with commercially available Hansen's yogurt culture. The initial inoculum of the Propionibacterium was either 1, 2, 4, or 10 ml of the mature cultures. At the end of 12 hours, the pH values were, respectively, 5.5, 5.9, 5.2, and 4.2. A small amount of carbon dioxide was produced during this time period as determined by visual observation. Each of these media was then inoculated with 1 ml of Hansen's yogurt culture and the milk was allowed to incubate for an additional 8 hours. At the end of this time, the pH values of the samples were, respectively, 4.5, 4,4, 4.5, and 4.6 and the viscosity, texture and flavor of the yogurt were very good.

In addition, an experiment was conducted wherein 10 ml of Propionibacterium was inoculated into the nonfat dry milk, allowed to incubate for 12 hours, and then heated to 85 C for 40 minutes to kill the propionibacteria and then cooled to inoculation temperature and inoculated with Hansen's yogurt culture. This also produced an excellent yogurt with very high viscosity and smooth, fine texture. Thus, it has been demonstrated here that in the production of yogurt, the milk could be preincubated with propionibacteria and then inoculated with yogurt producing cultures either with or without pasteurization in order to kill the propionibacteria, and an excellent quality yogurt can be produced.

Since propionibacteria are known to grow slowly at refrigeration temperature, as described by Hettinga and Reinbold, "The Propionic-Acid Bacteria-A Review", *J. Milk Food Technol.*, 35:295-30 (1972), this example teaches propionibacteria can be grown to substantial numbers in milk and then yogurt cultures can be added to produce yogurt, and then the product could be stored in the refrigerator and, with time, viable propionibacteria could produce metabolites which would be inhibitory to the development of mold and yeast or some bacteria as taught elsewhere herein.

A similar effect could be obtained by inoculating yogurt milk with large numbers of Propionibacterium cells immediately prior to inoculation with yogurt bacteria. The large number of propionibacteria might be obtained either by concentration or growing to large numbers with internal or external naturalization of the culture media. There is no teaching in the prior art that propionibacteria can be used either by preincubation or by simultaneous inoculation with yogurt producing bacteria in order to produce a good quality yogurt which would be inhibitory to yeast or spoilage bacterial growth.

EXAMPLE 14

Yogurt was prepared by pasteurizing 2 percent milk at 90° C. for 5 minutes, cooling to 30° C. and pouring 200 ml each into different autoclaved clear, plastic, 8 oz wide mouth jars with screw top caps. Nonfat dry milk powder (9 gm) and sucrose (11.5 gm) were added to each cup and mixed well by shaking.

Each cup was placed in a constant temperature water bath (42°-44° C.) and sterile, disposable pipets were used to inoculate with cultures as shown in the following tables. The screw-top caps were tightened, container contents mixed well by shaking, and the water bath temperature adjusted to 35° C. ± 0.5° C., and the inoculated samples were incubated overnight.

Samples were collected the next morning and allowed to stand undisturbed, without opening the caps, at room temperature or in the refrigerator as indicated in the following tables. Each sample was visually inspected (through the clear plastic cup) periodically for the development of mold, sample viscosity and gas formation as evidenced by bubble formation. The results are given in Tables XVII and XVIII.

The data in Table I show that the inclusion of propionibacteria along with usual yogurt-producing organisms allows production of a good consistency yogurt which can retain a good consistency if there is an appropriate balance in the amount of each culture used. This balance is an easy matter for one skilled in the art, now that this invention is disclosed. Those samples which developed gas bubbles may be desirable products if the gas production is not excessive since the appearance is not unpleasant and might be useful in marketing "Swiss-style" yogurt.

The room temperature data also show that mold developed in 7 days in the control sample (A-7) but was delayed by incorporation of propionibacteria until the 13th day or longer. This "doubling" of the "shelf-life" is a substantial improvement.

The data in Table II confirm the data in Table I in that the presence of propionibacteria increase substantially the length of time prior to appearance of mold; also the growth of mold, once it does appear, is much more rapid or "heavier" in the controls without propionibacteria.

Gas chromatographic data indicate that not much propionic acid was produced in these products. The data are shown below, and no anti-mold effects would be expected since bread is recommended to contain 2000-3000 parts per million to inhibit mold.

TABLE XVII

Results of storage at room temperature (20°-22° C.) of yogurt made with commerically-available yogurt cultures and ATCC 9617 Propionibacterium.

| ID No. | Inoculation | 1 | 2 | 3 | 4 | 5 | 6 | 7 | 8 | 9 | 10 | 11 | 12 |
|---|---|---|---|---|---|---|---|---|---|---|---|---|---|
| A-1 | (1 ml 9617 + 1 ml YC) | − | − | − | − | − | − | − | − | − | − | − | − |
| A-2 | (2 ml 9617 + 1 ml YC) | − | − | − | − | − | − | − | − | − | − | − | − |
| A-3 | (3 ml 9617 + 1 ml YC) | − | − | − | − | − | − | − | − | − | − | − | − |
| A-4 | (5 ml 9617 + 1 ml YC) | − | − | − | − | + | + | + | + | + | + | + | + |
| A-5 | (3 ml 9617 only) | − | − | − | + | + | + | + | + | + | ++ | ++ | ++ |
| A-6 | (2 ml 9617 only) | − | − | − | + | + | + | + | + | + | + | + | + |
| A-7 | (1 ml YC only) | − | − | − | − | − | − | − | − | − | − | − | − |
| A-7 (mold) | | | | | | | | M | M | M | M | M | M |

| ID No. | 13 | 14 | 15 | 16 | 17 | 18 | 19 | 20 | 21 | 22 | 23 | 24 | 25 |
|---|---|---|---|---|---|---|---|---|---|---|---|---|---|
| A-1 | − | − | − | − | − | − | − | − | − | − | − | − | − |
| A-1 (mold) | | | | | | | | M | M | M | M | M | M |
| A-2 | − | − | − | − | − | − | − | − | − | − | − | − | − |
| A-2 (mold) | M | M | M | M | M | M | M | M | M | M+ | M+ | M+ | M+ |
| A-3 | − | − | − | − | − | − | − | − | − | − | − | − | − |
| A-3 (mold) | | | | | M | M | M | M | M | M | M+ | M+ | M+ |
| A-4 | + | ++ | ++ | ++ | ++ | ++ | ++ | ++ | ++ | ++ | ++ | ++ | ++ |
| A-5 | ++ | ++ | ++ | ++ | ++ | ++ | ++ | ++ | ++ | ++ | ++ | ++ | ++ |
| A-6 | + | + | + | + | + | + | + | + | + | + | + | + | + |
| A-7 | − | − | − | − | − | − | − | − | − | − | − | − | − |

TABLE XVII-continued

| | | | | | | | | | | | | |
|---|---|---|---|---|---|---|---|---|---|---|---|---|
| M | M+ | M+ | M+ | M+ | M+ | M+ | M+ | M+ | M+ | M+ | M+ | M+ |

YC - Commerically-available yogurt cultures from Chr. Hansen's. Milwaukee. WI.
9617 - American Type Culture Collection - *Propionibacterium shermanii* strain 9617.
- - No bubble or "eye" formation.
+ - Few bubbles or "eyes".
+ + - Many bubbles.
M - First appearance of mold on the surface which was seen each day thereafter.
M+ - Heavy mold. The transition from slight to heavy mold is a subjective evaluation and no attempt was made to record increments of transition.
Both samples A-5 and A-6 produced poor products initially in terms of viscosity and separated early. The other products all had good viscosity initially, and samples A-1, A-2, A-3, and A-7 all had good viscosity even after 30 days at room temperature. Sample A-4 lost it physical consistency during extensive gas bubble production.

TABLE XVIII

Results of storage at refrigeration temperature (0°–4° C.) of yogurt made with commerically-available yogurt cultures and ATCC 9617 Propionibacterium.

| | | Days and observation of $CO_2$ (bubbles) | | | | | | | | | | | | | | |
|---|---|---|---|---|---|---|---|---|---|---|---|---|---|---|---|---|
| ID No. | Inoculation | 1 | 2 | 3 | 4 | 5 | 6 | 7 | 8 | 9 | 10 | 11 | 12 | 13 | 14 | 15 |
| B-1 | (1 ml 9617 + 1 ml YC) | - | - | - | - | - | - | - | - | - | - | - | - | - | + | + |
| B-2 | (2 ml 9617 + 1 ml YC) | - | - | - | - | - | - | - | - | - | - | - | - | - | - | - |
| B-3 | (3 ml 9617 + 1 ml YC) | - | - | - | - | - | - | - | - | - | - | - | - | - | - | - |
| B-4 | (5 ml 9617 + 1 ml YC) | - | - | - | + | + | + | + | + | + | + | + | + | + | + | + |
| B-5 | (3 ml 9617 only) | - | - | - | - | - | - | - | - | - | - | - | - | - | - | - |
| B-6 | (2 ml 9617 only) | - | - | - | - | - | - | - | - | - | - | - | - | - | M | M |
| B-7 | (1 ml YC only) | - | - | - | - | - | - | - | M | M | M | M | M | M | M | M |

| | Days and observation of $CO_2$ (bubbles) | | | | | | | | | | | | | | |
|---|---|---|---|---|---|---|---|---|---|---|---|---|---|---|---|
| ID No. | 16 | 17 | 18 | 19 | 20 | 21 | 22 | 23 | 24 | 25 | 26 | 27 | 28 | 29 | 30 |
| B-1 | + | + | + | + | + | + | + | + | + | + | + | + | + | ++ | ++ |
| B-2 | - | - | - | - | - | - | - | - | - | - | - | - | - | - | - |
| B-3 | - | - | - | - | - | - | - | - | - | - | - | - | - | - | - |
| | | M | M | M | M | M | M | M | M | M | M | M | M | M | M |
| B-4 | + | + | + | + | + | + | + | + | + | + | + | + | + | + | + |
| B-5 | - | - | - | - | - | - | - | - | - | - | - | - | - | - | - |
| B-6 | - | - | - | - | - | - | - | - | - | - | - | - | - | - | - |
| | M | M | M | M | M | M | M | M | M | M | M | M | M | M | M |
| B-7 | - | - | - | - | - | - | - | - | - | - | - | - | - | - | - |
| | M | M+ | M+ | M+ | M+ | M+ | M+ | M- | M+ | M+ | M+ | M+ | M+ | M+ | M+ |

YC - Commerically-available yogurt cultures from Chr. Hansen's. Milwaukee. WI.
9617 - American Type Culture Collection - *Propionibacterium shermanii* strain 9617.
- - No bubble or "eye" formation.
+ - Few bubbles or "eyes".
+ + - Many bubbles.
M - First appearance of mold on the surface which was seen each day thereafter.
M+ - Heavy mold. The transition from slight to heavy mold is a subjective evaluation and no attempt was made to record increments of transition.

TABLE XIX

| Sample Identification Number | Parts per Million of Propionic Acid |
|---|---|
| A-7 Controls | 11.9 |
| B-7 | 7.9 |
| A-2 | 6.9 |
| A-4 | 9.5 |
| B-2 | 16.7 |

This example teaches that Propionibacteria can be incorporated in the production of yogurt and will extend the shelf-life of the yogurt. They confirm data presented elsewhere herein which show the use of a food preservative additive comprising a mixture of metabolites of propionibacteria which is more inhibitory to mold than a weight of pure propionic acid which is equal to the pure propionic acid content of the metabolites. This example also shows the process of preserving a cultured dairy food product comprising selecting a Propionibacterium which produces a metabolite, other than propionic acid, which inhibits mold or yeast and providing the metabolite in the cultured dairy product in an amount sufficient for the metabolite to contribute to inhibition of the mold or yeast. This finding is certainly different from any previous suggestion that propionic acid (no matter what the source) can be incorporated in baked products. The literature does not contain any recommendations of standard amounts of propionic acid to add to cultured dairy products to inhibit mold in spite of the fact that standard recommendations have existed for addition to bread to inhibit mold for a long time. This is because propionic acid has such a distinctive flavor that it can not be used in the concentrations expected to be necessary to be effective.

EXAMPLE 15

*Propionibacterium shermanii* (ATCC Strain 9617) was grown in 800 ml of water containing either 62.4 g of a commercially available bulk starter medium (Formula 1-Phase 4, Galloway West Company, Fon Du Lac, Wisconsin) or in a formula (Formula 2) which contained in 800 ml of water, whey (28.8 g), yeast (4.0 g), diammonium phosphate (10 g), and citric acid monohydrate (1 g). Each formula was pasteurized at 85° C. for 45 minutes, and then cooled to 31° C. and inoculated with 10 ml of *Propionibacterium shermanii* 9617 which had been grown for 20 hours at 31° C. in milk. The organisms were allowed to incubate at 30° C. for 90 hours and at that time 1 ml and 5 ml samples of the growth media were transferred from each of the flasks and separately mixed with 20 ml of potato dextrose agar (29.25 g of potato dextrose agar in 500 ml of water) and the pH was reduced to 3.1 to 3.7 before pouring the plates. Three plates were made for each dilution and they were dried overnight at room temperature, inoculated 24 hours later with 0.2 ml of mold and 0.2 ml each of two different types of yeast. Yeasts and mold had been isolated from commercially available yogurt. These plates were then incubated at 31° C. for 48 hours. The results were the same for the two formulae tested in that 1 ml of the growth media did not inhibit yeast or mold and 5 ml of the growth media did not inhibit yeast but did inhibit mold growth. After 5 days, there was no growth of mold on any of the plates which had been inoculated with 5 ml of the growth media. It should be noted that control plates supported growth of mold and yeast after only 30 hours.

The above growth media which had been allowed to grow for 90 hours were allowed to continue to grow for an additional 10 hours and then the pH was raised to between 7.5 and 8.0 with a slurry of calcium hydroxide and the 800 ml of growth media for each formula was divided into two 400 ml portions and dried two different ways. The first 400 ml portion of each growth medium was evaporated to semidryness using a rotary evaporator and a water vacuum at a temperature of about 70° C. and then the powder was placed in a vacuum oven at 80° C. and dried; finally the powder was pulverized using a hammermill. The initially light cream colored growth medium produce quite a dark brown powder.

A quantity (300 ml) of each formula (1 and 2 above) was lyophilized by freeze-drying after 100 hours of growth. This produced a creamy white powder.

Powder (5 g of each of the above dried powders) was added to 50 ml of water and 3.9 g of potato dextrose agar was added to 50 ml of water and the liquids were autoclaved separately, mixed together, and the pH was lowered to 3.6 using hydrochloric acid before the plates were poured. Plates were then allowed to dry overnight at room temperature. Three plates were made for each powder and 0.2 ml of yeast (two separate types) and 0.2 ml of mold were each transferred to each plate as a spread plate. The mold and yeast had been isolated from a commercially available contaminated yogurt sample as one loopful of culture which was transferred as a 0.2 ml sample to each plate. Plates were then incubated at 31° C. for 40 hours. The results were quite spectacular in that there was no growth of either type of yeast or of mold on any of the plates which contained either the freeze-dried or the heat dried powder. However, there was extensive mold and yeast growth on the control plates.

Yogurt was prepared by using 200 ml of 2 percent milk and following the usual procedures for preparation of yogurt with inoculation of 0.5 ml of commercially-available Hansen's yogurt producing bacteria. The incubation temperature was 35° C. for 17 hours. The control sample was fortified with 9 g of whey and 11.5 g of sucrose; 20 percent of a commercially available strawberry fruit flavor was added after the yogurt was formed. A "plain" control was also prepared which did not have the added fruit flavor. In addition, a control fortified with 9 g of nonfat dry milk and 11.5 g of sucrose with added fruit flavor was also prepared. The initial pH of each of these preparations was 6.45 to 6.5 and the final pH was 4.15 to 4.4. Each produced a very smooth, uniform yogurt product with an excellent consistency and each of these exhibited mold growth on the surface beginning between the 4th and 5th day after production of the yogurt.

A yogurt formula was also prepared containing the same ingredients as the control above except that 9 g of whey was replaced with 7 g of whey plus 2 g of the heat dried powder produced by growing Propionibacterium in Formula 1. Flavor was also added after formation of the yogurt. The initial pH of the milk before formation of yogurt was 6.5 and the final pH was 4.6. The final product was discolored because the heat dried powder was discolored and the product was somewhat separated and was not uniform in viscosity. Mold growth was inhibited and did not appear on the surface of this formula until the 7th day.

An additional yogurt sample was prepared which contained only 1 g of Formula 1 and 8 g of whey and this product was very similar to the preceding product in appearance and the mold did not appear on the surface of this product until the 8th day. It should also be noted that there appeared to be some yeast present since carbon dioxide was slowly evolved from this product.

Yogurt was also prepared which contained 6.3 g of the heat dried powder from Formula 2 identified above and this product was prepared in 200 ml of 2 percent milk which had been fortified with 11.5 g of sucrose. After preparation, the fruit flavor was added. This product had an acceptable consistency and did not show any evidence of mold growth by the 8th day.

The freeze dried powders identified above were also used to produce yogurt. The control yogurt was made from 200 ml of 2 percent milk fortified with 9 g of whey and flavor was added after production. In addition, a control was prepared which was not flavored and a control was prepared which was fortified with 9 g of nonfat dry milk and was flavored. All controls produce excellent products and developed mold growth after the th day of storage at room temperature.

The samples containing the freeze dried powder were all flavored after production and were all made from 200 ml of 2 percent milk. The first sample was fortified with 4½ g of whey and 4½ g of powder which had been freeze dried and was produced by growing the Propionibacterium in a commercially-available medium (Formula 1). The second sample contained 2 g of the same freeze dried powder and 7 g of whey; the third sample contained 4½ g of the freeze dried powder from Formula 2 above and 4½ g of whey; the fourth sample was fortified with 2 g of the freeze dried powder form Formula 2 above, and 7 g of whey. In all of these cases, a product with excellent consistency was formed and there was no apparent yeast or mold growth after 6 days in any of these products treated with the freeze dried powders. The color was much better than when the powder had been heat dried although there was some odor which appeared to be from the whey base growth media in these final products.

This present example shows that a product can be produced b growing propionibacterium on whey base media which, after drying, will be effective inhibiting yeast and mold growth in dairy products.

It is apparent from other examples herein that the Propionibacteria can be grown in nonfat dry milk and a product with a very acceptable odor and color can be produced after drying the growth media.

FIG. 1 shows six plates of acidified (pH 3.5) potato dextrose agar. The two plates on the left were inoculated with mold, the center two with yeast, and the two on the right with mold and yeast. Control plates (top row) with no inhibitor have substantial growths of mold and/or yeast. Plates (bottom row) with 5 percent added, powdered growth mixture of *P. shermanii* sustained no growth.

EXAMPLE 16

In 800 ml of water was prepared whey (100 g), yeast extract (5 g), and diammonium phosphate (8 g) and this is referred to as Formula 1 for this example. Formula 2 for this example consisted of whey (100 g), yeast (5 g), and diammonium phosphate (12 g). Each formula was pasteurized at 85° C. for 45 minutes, the temperature was allowed to cool to 35° C., and the growth media were then inoculated with 10 ml of *Propionibacterium shermanii* (10 ml) strain 9617 which had been grown in sodium lactate broth. These culture media were allowed to grow for 90 hours and then 5 ml of each culture was mixed separately with 20 ml of potato dextrose agar (19.5 g for 250 ml) and the pH was lowered to 3.4 using hydrochloric acid before the plates were poured. Three plates were made for each formula. Plates were dried overnight and then inoculated with 0.2 ml of either mold or each of two different kinds of yeast and then incubated for 24 hours at 31° C. Yeast and mold growth appeared on control plates within 36 hours but yeast did not appear on any of the plates containing the growth media until after 6 days, and mold did not appear on any of the plates containing growth media for up to 10 days.

The culture was allowed to continue to grow for an additional 6 hours or a total of 96 hours and then the samples were divided and a portion of each growth medium was freeze dried and a portion was heat dried. The powders so prepared were mixed (5 g of powder plus 50 ml of water) with potato dextrose agar (3.9 g of agar plus 50 ml of water). It should be noted that the pH of the growth cultures was not raised before drying, which is different from a previous example. Each of the solutions prepared were autoclaved and then the potato dextrose agar and the freeze dried or heat dried powder solutions were combined, the pH of each plate was adjusted to 3.0 to 3.6 with hydrochloric acid, and the plates were poured. After drying, each plate was inoculated with 0.2 ml of yeast or 0.2 ml of mold, and the plates were incubated for 72 hours at 31° C. It should be noted that the pH of some of the dried powder plus water solutions was raised to about 7.5 prior to autoclaving and the pH was not raised up to 7.5 before autoclaving for some other preparations.

When the pH of the heat-dried powder plus water mixture was increased prior to raised prior to autoclaving, there was complete inhibition of yeast and mold for both Formulas 1 and 2 prior to 72 hours and then some mold did appear on the plates after 72 hours of incubation.

For the freeze dried powder (Formula 2) when the pH was not autoclaving, the plates were negative for yeast and mold for at least 48 hours.

For the freeze-dried powder when the pH was raised prior to raised prior to autoclaving, the plates were negative for both yeast and mold for 48 hours.

The growth medium, which had not been dried, was centrifuged to provide two fractions of different densities. The low density fraction, i.e. the supernatant, was filtered through a 0.22 micron diameter pore size filter and 5 ml of the filtrate for each formula was mixed with potato dextrose agar and the plates were inoculated as indicated above. The filtrates were inhibitory to both yeast and mold as indicated by a more rapid growth of yeast and mold on control plates than with those plates which contained filtrate. After 72 hours, the supernatant from formula 1 above did allow the growth of yeast and was marginal with respect to slight growth of mold. However, the supernatant from Formula 2 completely prevented yeast and mold growth for the entire 72 hours.

This experiment shows clearly that propionibacteria growth medium can be converted to a dry powder either by heat drying or freeze drying and the powder produced will inhibit yeast and mold. In addition, this example demonstrates that the growth medium supernatant liquid contains inhibitory substance(s) which can be used to inhibit yeast and mold.

EXAMPLE 17

Yogurt was prepared by inoculating 200 ml of 2 percent milk fortified with nonfat dry milk (4.5 g) and sugar (11.5 g) as a basal formula. Commercially available yogurt cultures (Hansen's) were used.

Propionibacterium (strain 9617) was grown for 96 hours in a mixture of whey (200 g), diammonium phosphate (12 g), and yeast extract (5 g), in 800 ml of water (identification symbol p-a) or in a formula of nonfat dry milk (200 g), diammonium phosphate (12 g), yeast (5 g), in 800 ml of water (identification p-b). Each of these growth media were then either freeze dried or heat dried as described elsewhere herein. The following combinations of ingredients were then used to prepare yogurt. The basal media also initially contained sodium caseinate (1.0 g) unless specified otherwise below and in some cases a fruit flavor (10.0 g) was added after the yogurt had been formed. The following 12 formulae were tested.

1) Basal medium plus p-a (4.5 g) which had been freeze dried,
2) Basal medium plus p-a (4.5 g) which had been heat dried,
3) Basal medium plus p-a (4.5 g) which had been freeze dried and no flavor,
4) Basal medium plus p-a (4.5 g) which had been heat dried and no flavor,
5) Basal medium plus p-a (4.5 g) which had been heat dried and no sodium caseinate,
6) Basal medium plus p-a which had been heat dried, 4.5 g and no sodium caseinate and no flavor,
7) Basal medium plus p-b which had been freeze dried, 4.5 g,
8) Basal medium plus p-b which had been heat dried, 4.5 g,
9) Basal medium plus p-b which had been freeze dried, 4.5 g and no flavor,
10) Basal medium plus p-b which had been heat dried, 4.5 g and no flavor,
11) Basal medium plus p-b which had been heat dried, 4.5 g and no sodium caseinate,
12) Basal medium plus p-b which had been heat dried, 45. g and no sodium caseinate and no flavor.

Each of the above products produced an excellent yogurt with excellent viscosity and texture. Those yogurts which had been prepared with p-b often had a solid or precipitate on the bottom which was readily dispersed and mixable with the products which contained flavor since the stirring of the flavor into the yogurt distributed any solid which had settled to the bottom. It is possible that the source of the solid was coagulated proteins which developed during the growth of Propionibacterium prior either to freeze drying or heat drying of the growth medium when nonfat dry milk was used as part of the nutrient medium, since a layer of solid or precipitated material did not develop in those formulae prepared with p-a which employed whey rather than nonfat dry milk.

The above products were prepared and stirred and three additional cups of yogurt which were purchased commercially were placed in identical containers and stirred and set out with these 12 products for a taste test by 3 individuals experienced in dairy microbiology and yogurt production. Combined, these individuals had 50 years experience in working with dairy products and have been involved in taste panels for judging yogurt. In general, the products prepared in this example were judged to be equal to the commercially-purchased products, and the preferred formulae were numbers 3, 4, 5, and 12 although the three "taste experts" did not agree on the order of superiority.

These products were kept in the refrigerator and examined daily. A commercially available flavored product exhibited large amounts of gas production and a yeasty odor and flavor 6 days after purchasing. A plain yogurt which had been purchased showed growth of mold on the surface after 20 days in the refrigerator. An additional flavored yogurt which had been purchased also showed physical separation and had a very bad yeasty odor. There was no appearance of yeast in the formulas 1-12 above after 26 days and the first appearance of mold appeared on the surface of a few samples after 26 days. Most of the samples did not exhibit mold or yeast growth for a prolonged period although the exact appearance date of contamination was not recorded in this experiment.

FIG. 2 shows three containers of yogurt which were held for 30 days at 50° F. The two containers at the bottom without inhibitor have substantial growth of surface mold. Yogurt in the top container, with 2.5% added powdered growth mixture of *P. shermanii*, had no surface mold.

In a separate experiment with similar formulations stored at room temperature, mold often appeared on the surface of control formulations in four or five days for products which had been flavored but those which contained 2.25% of the powdered growth medium of propionibacteria did not demonstrate mold growth until almost three times as long (i.e. 12 to 14 days) and in one exceptional case mold appearance was delayed for over 40 days, even though the container was opened and checked daily.

EXAMPLE 18

Kissle-type Products

"Kissle" is a registered trademark for a commercially available, noncultured yogurt substitute. The product contains milk, cream, stabilizers, carbohydrates and protein. Chocolate, apricot, and blueberry lavored Kissle products were obtained commercially; and each was divided into controls and test samples.

The controls developed gas bubbles at room temperature after three days and mold developed on the top of the chocolate and apricot control Kissle product after five days, although mold did not appear in the blueberry product at that time. In addition, the chocolate flavored control developed mold after 16 days in the refrigerator and the apricot flavored product developed mold after 21 days in the refrigerator.

The test samples were incorporated with 2¼% of powder produced by drying propionibacterium growth medium as described in Example 15 herein, and the products were then stored at either room or refrigeration (2°-5° C.) temperature in a study design which paralleled the controls described in the above paragraph. After 30 days, there was no mold or yeast in any of the Kissle products which had the dried, powdered propionibacteria growth medium added at either room temperature or refrigeration temperature. This example further indicates that the materials produced by growing propionibacterium can be effective at inhibiting both yeast and mold in dairy products. The appearance, odor and flavor of these products with the extended shelf-life were all excellent.

EXAMPLE 19

Fruit Juice

The shelf life of a variety of fruit juices and related products was extended using propionibacteria according to the present invention.

Apple cider which had been filtered prior to packaging and another sample which had not been filtered, grape juice frozen concentrate, concentrated raspberry yogurt flavor and concentrated cherry yogurt flavor for use in yogurt were commercially obtained. Small paper cups were prepared containing about 100 g of each type of apple cider and of the concentrated grape juice and of the grape juice after it had been diluted according to manufacturer's instructions, and the cherry yogurt flavor and the raspberry yogurt flavor.

Five cups of each were prepared with one cup of each serving as a control. Other cups were inoculated with yeast and/or mold obtained from commercial yogurt. The second cup of each food product was inoculated with 1 ml of viable yeast cells only; and a third cup was inoculated with 1 ml of viable mold only. The fourth cup was inoculated with 1 ml of viable yeast and 3% of a heat-dried powder produced from growing Propion:bacteria medium according to Example 15, and the fifth cup was inoculated with 1 ml of viable mold and 3% of the powdered Propion:bacteria growth medium. These were then stored at room temperature (uncovered). The following key was used to identify the effects:

| | |
|---|---|
| 1. Apple cider, filtered | a. Mold |
| 2. Unfiltered apple cider | b. Yeast |
| 3. Diluted grape juice | c. Mold plus *Propionibacterium* growth medium |
| 4. Concentrated grape juice | d. Yeast plus *Propionibacterium* growth medium |
| 5. Raspberry yogurt flavor | e. Control |

On the second day, cup 1-b (apple cider filtered and inoculated with yeast) developed a yeasty odor and cup 3-b (diluted grape juice inoculated with yeast) also developed a yeasty odor. On the third day, cup 1-a developed mold and cup 3-a also developed mold, and cup 4-b (concentrated grape juice inoculated with yeast) developed yeast. On the 4th day cup 1-3 had mold, and cup 4-a had mold. However, cups c and d which were the products inoculated with mold and yeast and the powdered Propionibacterium growth medium did not have any mold or yeast even after four days at room temperature as contrasted to those samples which did not contain the Propionibacterium growth medium as described above.

This demonstrates a dramatic usefulness of the Propionibacterium growth medium in inhibiting yeast and mold in a variety of food products.

EXAMPLE 20

*P. shermanii* ATCC 9616 was grown in frozen-reconstituted orange juice fortified with 0.1% yeast extract for two days at 30° C. A commercial orange juice concentration was diluted 50%, 10%, 5% and 1%. The pH was adjusted to 5.0 with 1.0 molar NaOH. Three sets of the above dilutions were made. One set was autoclaved, the second set pasteurized, and the third set received no heat treatment. The three sets were inoculated with 5% *P. shermanii* culture and incubated at 30° C. for five days. Centrifugation was carried out on all the three sets and the supernatant was filter sterilized and used (5%) against four different molds. Controls were made from the orange juice receiving the above treatment without *P. shermanii* inoculation but inoculated with the different molds.

Results appear in Table XX:

propionic acid which has an inhibitory effect on yeast spoilage organisms, and the material can be provided in a food product in an amount sufficient to inhibit the spoilage yeast. These data further show the preservation of a food product with a propionibacteria fermented medium that contains insufficient propionic acid to preserve the food product. The above is clear as the sour cream contains only 0.02% propionic acid and 10 times that amount (0.2%) is commonly used in yeast raised dough baking products and does not inhibit the yeast.

TABLE XXI

| | YEAST RESULTS | | | | |
|---|---|---|---|---|---|
| | 0 Day | 7 Day | 14 Day | 21 Day | 33 Day |
| Control | 60 | 1080 | 21,800 | 78,000 | 109,000 |
| Metabolite Mix | 90 | 100 | 510 | — | 24,200 |

To assay against mold growth, one carton each of control and metabolite-containing sour cream was distributed evenly among six sterile petrie dishes using aseptic technique. These plates were kept at 45° F. and observations were made every day to note the first sign

TABLE XX

| Mold strain | Days | Autoclaved | | | | Pasteurized | | | | Untreated | | | | Control |
|---|---|---|---|---|---|---|---|---|---|---|---|---|---|---|
| | | 50% | 10% | 5% | 1% | 50% | 10% | 5% | 1% | 50% | 10% | 5% | 1% | |
| A. niger | 3 | —[a] | — | — | — | — | — | — | — | + | + | + | + | + |
| P. cyclopium | | — | — | — | — | — | + | + | — | + | + | + | + | + |
| P. roquiforti | | +[b] | + | + | + | — | + | + | + | + | + | + | + | + |
| F. oxysporum | | — | — | — | — | — | — | — | — | — | + | + | + | + |
| A. niger | 21 | + | — | — | + | — | — | — | — | + | + | + | + | + |
| P. cyclopium | | — | — | — | — | — | — | — | — | + | — | + | + | + |
| P. roquiforti | | + | + | + | + | — | + | + | + | + | + | + | + | + |
| F. oxysporum | | — | — | — | — | — | — | — | — | + | + | + | + | + |

[a] — means inhibition.
[b] + means growth.
These results show that propionibacteria produce metabolites inhibitory to yeast and mold when growth in orange juice.

EXAMPLE 21

Two vats of sour cream were manufactured at a commercial dairy plant. Prior to pasteurization of the starting cream, one vat had a Propionibacterium metabolite mixture added at a level of 1.0%. The metabolite mixture had a concentration of propionic acid of 20,700 ppm, and acetic acid at a concentration of 13,100 ppm, as determined by gas chromatography prior to the addition which produced a propionic acid concentration of 0.02% in the sour cream.

After pasteurization, the cream was inoculated with gram positive starter organisms and incubated for 12 hours. The sour cream developed normally, and the starter culture bacteria were not inhibited by the Propionibacterium metabolite mixture. The sour cream was then packaged by machine in one pound cartons and cooled to 45° F. Cartons from the vat without the added metabolite mixture were used as controls.

To monitor the growth of spoilage yeast present, samples of control- and metabolite-containing sour cream were plated at various times. Dilutions of each sample were plated with Potato-Dextrose agar (acidified with tartaric acid) using standard pour plate technique. Plates were incubated for 3 days at 30° C., then counted. The results, which appear in Table XI, show viable yeast cells per gram of sour cream have multiplied to much higher numbers in sour cream without the metabolite mixture.

Since propionic acid concentrations of 0.02% are not known to inhibit yeasts, this example shows that propionibacteria produce at least one metabolite other than of mold. This method was used as it is difficult to accurately enumerate mold. To a consumer, the appearance of mold is of more significance than numbers of mold spores present. The data appear in Table XXII.

TABLE XXII

| MOLD RESULTS: Days after preparation that mold first appeared on sour cream samples | | |
|---|---|---|
| Petrie Dish | Control Sample without Metabolite Mix | Sample with Metabolite Mix |
| 1 | 35 | 38 |
| 2 | 21 | * |
| 3 | 16 | 38 |
| 4 | 21 | * |
| 5 | 24 | 34 |
| 6 | 27 | 46 |

*Petrie dishes 2 and 4 containing sour cream did not show any visible mold growth, even after 46 days.

Based on the gas chromatographic results, the use of the metabolite mixture provided only 0.02% propionic acid in the sour cream. Thus, these results are surprising since the literature suggests 10 times that amount of propionic acid (0.2%) is needed to inhibit mold. These results show that propionibacteria produce one or more metabolites, other than propionic acid, which have an inhibitory effect on mold such that a material containing the metabolite or metabolites other than propionic acid can be provided to a food in an amount sufficient for the metabolite or metabolites to inhibit mold more effectively than an amount of pure propionic acid equivalent to any propionic acid which is actually present with other metabolites. In this case, the propionibacteria metabolites are more effective to inhibit mold than 0.02% propionic acid.

EXAMPLE 22

Six different strains of Propionibacterium were grown in a commercially available (PHASE 4, Galloway-West Co., Fond Du Lac, Wis.) whey-based bulk starter medium that contains yeast extract as a growth stimulant. Six containers were prepared by adding 39 g of the medium to 500 ml of water, pasteurizing at 85° C. for 45 minutes, and cooling to 30° C. Each was then inoculated with 10 ml of one of 6 different cultures grown in tomato juice media for 24 hours. The Propionibacterium cultures tested were: p-31-c; 13673; 8262; 9615; 9616; 9617. These were all obtained from the American Type Culture Collection in Rockville, Md.

After times 0, 16, 18, 21, and 24 hours, 25 ml of the growth media were removed by pipette, mixed with 25 ml of double strength potato dextrose agar (39 g for 500 ml of water) and the mixture was autoclaved. After the potato dextrose agar and sample were mixed, the sample was brought down to pH 3.0 to 3.7 with hydrochloride acid and poured into plates. The plates were dried overnight and then mold or yeast was streaked onto each plate the next day and the plates were incubated at 33° C. for 24 hours. Plates containing the zero hour Propion:bacteria growth medium showed a large amount of growth of mold and yeast. The samples collected at 16, 18, 21, and 24 hours all allowed the growth of yeast (most after 24 hours) but mold was inhibited on these plates, even though the samples collected and used for zero hour plates did have extensive mold growth.

For p-31-c, yeast was apparent after 20 hours and there was no mold for 60 hours. For 13673, yeast Was present after 24 hours and no mold was apparent after 72 hours. For 8262, there was both yeast and mold after 24 hours. For strains 9615, 9616, and 9617, yeast was present after 24 hours; but no mold appeared during 72 hours of observation. Samples of growth media containing 9617 were somewhat inhibitory to yeast in this experiment as indicated by less growth of yeast on plates containing samples of 9617.

Duplicates of the above plates were prepared after continuing to grow the propionibacteria from 24 up to 80 hours and utilizing samples collected at times 0, 16, 18, 21, 24, and 80 hours after beginning of growth. Each plate was divided into 3 parts and 1 part was streaked with mold and the other two parts were each streaked with 2 different kinds of yeast. The results for these duplicate samples showed that for strain p-31-c, none of the samples prevented complete growth of yeast or mold, except the 18-hour sample which prevented mold growth. For strain 13673, the 80-hour sample was inhibitory to mold, but none of these other samples presented yeast or mold growth. For strain 8262, none of these samples were inhibitory to mold or yeast. For strain 9615, the 24-hour sample and the 80-hour sample were inhibitory to mold and the 80-hour sample was inhibitory to yeast. For strain 9616, the 80-hour sample was inhibitory to mold and slightly inhibitory to yeast. For strain 9617, the 24-hour and 80-hour samples were inhibitory to yeast and the 18, 21, 24 and 80-hour samples were all inhibitory to mold.

These data show that strains 9615, 9616, 9617, and 13673 which have been allowed to grow for 80 hours under the conditions described herein can inhibit growth of mold or both yeast and mold, and that strains 9616 and 9617 were most active in inhibiting yeast and mold.

An additional experiment was conducted wherein each of the cultures were sampled 18 hours after growth and 100 hours after growth and the samples which were collected were 1 ml and 5 ml and 10 ml of the growth medium at 18 hours and 1 ml and 5 ml at 100 hours. These samples were then mixed with 20 ml of potato dextrose agar (58.5 g for 1000 ml, autoclaved and poured into plates after adjusting the pH to between 3.0 and 3.6 using concentrated hydrochloric acid). The plates were dried overnight and inoculated as spread plates with 0.2 ml of each of 2 different kinds of yeast or with mold. Plates were then incubated at 30° C. for 30 hours. Results showed that 10 ml of strain 9615 was inhibitory to mold after 18 hours of growth and 10 ml of strain 9617 was inhibitory to mold after 18 hours of growth. The other samples were not inhibitory after only 18 hours of growth. However, after 100 hours of growth, strain 13673 was inhibitory to mold and yeast for the 5-ml sample and to mold with the 1-ml sample. Strain p-31-c was not inhibitory. Strain 8262 was inhibitory to mold with the 5-ml sample. Strain 9617 was inhibitory to mold with the 1-ml sample and inhibitory to both yeast and mold with the 5-ml sample. It should be noted that the most inhibitory to mold of all these strains was 9616 where 1 ml of the growth medium inhibited the growth of molds on the plates for over 75 hours, which is longer than any of the other growth media inhibited mold at such a low concentration. Control plates showed the presence of mold and yeast after only 30 hours of incubation.

Although the amount of propionic acid produced was not determined by analysis, Anderson (U.S. Pat. No. 4,497,833) suggests that probably less than 1% propionic acid was produced which would provide only 0.05% (for 1 ml to 20 ml dilution) propionic acid in the mold and yeast growth medium. Consistent with earlier examples, several of these mixtures of metabolites inhibited mold and some inhibited yeasts.

It is not known which of the propionibacteria metabolites and combinations of metabolites is most effective in the inhibition of undesired microorganisms. As mentioned above, propionic acid is suggested for use only to inhibit certain specific microorganisms, i.e. mold. Based on literature teachings, the amount of propionic acid produced cannot account for the great activity of metabolite mixtures, as mentioned in the examples.

While we have described and given examples of preferred embodiments of our inventions, it will be apparent to those skilled in the art that changes and modifications may be made without departing from our inventions in their broader aspects. We therefore intend the appended claims to cover all such changes and modifications as fall within the true spirit and scope of our inventions.

We claim:

1. A process for preserving a food product against a gram negative psychotropic bacteria comprising combining with a food product that is subject to spoilage by growth of a gram negative psychotropic bacteria, a metabolite-containing material that is produced by a culture of Propionibacterium and that contains a metabolite, other than propionic acid, the material being present in an amount sufficient that the metabolite inhibits the growth of gram negative psychotropic bacteria and that the material provides less than 0.02% propionic acid in the food product such that there is insufficient propionic acid per se to inhibit the growth of gram negative psychotropic bacteria.

2. The process of claim 1 wherein the food product is yogurt, cottage cheese, fruit juice, vegetable juice, ground meat, milk, half and half, whipping cream, sour cream, salad dressing, or pasta.

3. The process of claim 1 wherein the food product is a fermented product and wherein the material is provided by including a Propionibacterium culture in a batch before fermentation.

4. The process of claim 1 wherein the food product comprises creamed cottage cheese and the material is formed by providing viable propionibacteria in the cottage cheese cream.

5. The process of claim 1 wherein the material consists essentially of all the metabolites formed by growth of the culture.

6. The process of claim 1 comprising intimately mixing the material and the food product.

7. The process of claim 1 comprising applying the material to the surface of the food product.

8. The process of claim 1 comprising injecting the material into the food product.

9. The process of claim 1 wherein the material includes propionibacterial cells of the culture, at least some of the cells being viable.

10. The process of claim 1 wherein the material includes propionibacterial cells of the culture, the cells having been rendered not viable.

11. The process of claim 1 wherein the material is provided by growing the culture in a liquid growth medium to provide a liquid mixture containing the active metabolites.

12. The process of claim 11 further comprising concentrating, spray-drying or freeze-drying the liquid mixture so that the mixture, which includes the metabolites, can be added as a concentrated liquid or powder to the food product.

13. The process of claim 1 wherein the material is provided by:
growing the culture in a liquid growth medium to provide a liquid mixture containing the active metabolites;

14. The process of claim 1 wherein the material contains propionic acid.

* * * * *